US008481270B2

(12) United States Patent
Gniewek et al.

(10) Patent No.: US 8,481,270 B2
(45) Date of Patent: Jul. 9, 2013

(54) METHOD FOR CHROMOGENIC DETECTION OF TWO OR MORE TARGET MOLECULES IN A SINGLE SAMPLE

(75) Inventors: Richard Gniewek, Oro Valley, AZ (US); Michael Farrell, Tucson, AZ (US); Hiroaki Nitta, Oro Valley, AZ (US); Megan Lehrkamp, Castro Valley, CA (US); Jerome Kosmeder, Tucson, AZ (US); Brian Daniel Kelly, Tucson, AZ (US); Thomas Grogan, Tucson, AZ (US); Fabien Gaire, Oro Valley, AZ (US); Mary Padilla, Tucson, AZ (US); Christopher Bieniarz, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 233 days.

(21) Appl. No.: 13/059,274

(22) PCT Filed: Aug. 21, 2009

(86) PCT No.: PCT/US2009/054614
§ 371 (c)(1),
(2), (4) Date: Feb. 16, 2011

(87) PCT Pub. No.: WO2010/022332
PCT Pub. Date: Feb. 25, 2010

(65) Prior Publication Data
US 2011/0136130 A1 Jun. 9, 2011

Related U.S. Application Data

(60) Provisional application No. 61/189,752, filed on Aug. 22, 2008.

(51) Int. Cl.
*C12Q 1/68* (2006.01)
*G01N 33/58* (2006.01)
*G01N 33/53* (2006.01)

(52) U.S. Cl.
USPC ......... 435/6.19; 435/6.1; 435/6.11; 435/6.17; 435/7.1; 435/7.9

(58) Field of Classification Search
None
See application file for complete search history.

(56) References Cited

U.S. PATENT DOCUMENTS

| 6,949,342 B2 * | 9/2005 | Golub et al. | 435/6.14 |
| 2006/0160151 A1 * | 7/2006 | Allred et al. | 435/7.5 |

FOREIGN PATENT DOCUMENTS

| WO | WO 94/02830 | 2/1994 |
| WO | WO 98/02577 | 1/1998 |
| WO | WO 00/20641 | 4/2000 |
| WO | WO 2008/063378 | 5/2008 |

OTHER PUBLICATIONS

Hunyady et al., "Immunohistochemical signal amplification by catalyzed reporter deposition and its application in double immunostaining," J. Histochem. Cytochem., 1996, vol. 44, No. 12, pp. 1353-1362.*
Zaidi et al., "Dual Fluorescent in Situ Hybridization and Immunohistochemical Detection with Tyramide Signal Amplification," J. Histochem. Cytochem., 2000, vol. 48 No. 10, pp. 1369-1375.*
Moriuchi et al., "Use of non-radioactive DNA probes for the characterization of adult T-cell leukemia cells," Nucleic Acids Symp Ser., 1988, No. 19, pp. 77-80.*
Ambretti et al., "Assessment of the presence of mucosal human papillomaviruses in malignant melanomas using combined fluorescent in situ hybridization and chemiluminescent immunohistochemistry," *British Journal of Dermatology*, vol. 156, pp. 38-44, 2007.

* cited by examiner

*Primary Examiner* — Shafiqul Haq
*Assistant Examiner* — Galina Yakovleva
(74) *Attorney, Agent, or Firm* — Klarquist Sparkman, LLP

(57) ABSTRACT

The present invention provides a method and kit for detection of two or more target molecules in a single tissue sample, such as for gene and protein dual detection in a single tissue sample. Methods comprise treating a tissue sample with a first binding moiety that specifically binds a first target molecule. Methods further comprise treating the tissue sample with a solution containing a soluble electron-rich aromatic compound prior to or concomitantly with contacting the tissue sample with a hapten-labeled binding moiety and detecting a second target molecule. In one example, the first target molecule is a protein and the second is a nucleic acid sequence, the first target molecule being detected by immunohistochemistry and the second by in situ hybridization. The disclosed method reduces background due to non-specific binding of the hapten-labeled specific binding moiety to an insoluble electron rich compound deposited near the first target molecule.

35 Claims, 8 Drawing Sheets

| No Blocking | No EGFR Probe | Blocking |
| ● EGFR | | ● EGFR |
| ● CEN7 | ● CEN7 | ● CEN7 |
| ● Anthracotic pigment | ● Anthracotic pigment | ● Anthracotic pigment |

METHOD FOR CHROMOGENIC DETECTION OF TWO OR MORE TARGET MOLECULES IN A SINGLE SAMPLE

CROSS REFERENCE TO RELATED APPLICATION

This is the §371 U.S. National Stage of International Application No. PCT/US2009/054614, filed on Aug. 21, 2009, which was published in English under PCT Article 21(2), which in turn claims the benefit of U.S. Provisional Application Ser. No. 61/189,752, filed on Aug. 22, 2008, which is incorporated herein by reference in its entirety.

FIELD

This disclosure relates to immunohistochemistry (IHC) and in situ hybridization (ISH), and specifically to embodiments of a method for chromogenic detection of two or more target molecules in a single sample.

BACKGROUND

Immunohistochemistry (IHC) employs specific binding agents, such as antibodies, to detect an antigen of interest that may be present in a tissue sample. IHC is widely used in clinical and diagnostic applications, such as to diagnose particular disease states or conditions. For example, particular cancer types can be diagnosed based on the presence of a particular marker molecule in a sample obtained from a subject. IHC is also widely used in basic research to understand biomarker distribution and localization in different tissues.

Biological samples also can be examined using in situ hybridization (ISH) techniques, such as silver in situ hybridization (SISH), chromogenic in situ hybridization (CISH) and fluorescence in situ hybridization (FISH), collectively referred to as ISH. ISH is distinct from IHC, in that ISH detects nucleic acids in tissue sections whereas IHC detects proteins.

As IHC and ISH methods are becoming increasingly important in research and clinical settings, as is the ability to detect multiple targets at once, such as dual detection of a nucleic acid sequence and protein or multiple proteins or nucleic acids on a single sample. For example, a dual gene/protein detection system would allow gene and protein detection on the same slide in one automated run as opposed to two separate runs. However, current detection systems do not adequately provide for detection of multiple targets, such as dual gene/protein detection, on the same slide because IHC and ISH procedures are frequently incompatible with one another.

SUMMARY

The present invention provides for methods and kits for chromogenic detection of two or more target molecules in a sample. Further provisions of the present invention address non-specific background that occurs when performing a method for chromogenic detection of two or more target molecules in a single tissue sample. Thus, the present disclosure is particularly directed to any process and/or composition that facilitates dual detection while decreasing non-specific background. This may be achieved by substantially reducing or preventing non-specific binding of an electron-deficient aromatic compound (such as DNP) to an electron-rich chromogen complex during chromogenic detection of two or more target molecules in a single sample. Methods described herein may be automated or may be performed manually.

In an embodiment, a method for chromogenic detection of two or more target molecules in a single tissue sample includes contacting the tissue sample with a first specific binding moiety that specifically binds a first target molecule. In one example, the first specific binding moiety is a primary antibody and the first target molecule is a protein. For example, the primary antibody can be an antibody that detects a protein associated with cancer, such as a HER2/neu (or HER2 protein), c-Myc, n-Myc, Abl, EGFR protein, TOP2A, Bcl2, Bcl6, Rb1, p53, or c-Met primary antibody.

The particular embodiment for chromogenic detection also includes detecting the first target molecule in the tissue sample by depositing an insoluble, electron-rich aromatic chromogen product at or about the point where the first specific binding moiety is bound to the first target molecule. In one example, the insoluble, electron-rich aromatic compound is an azo dye. In some examples, depositing a chromogen product includes reacting a substrate with a catalyst to form the insoluble, electron-rich aromatic compound. For example, the catalyst may be an enzyme, such as alkaline phosphatase or horseradish peroxidase. Further, the substrate can be diaminobenzidine (DAB), 3-Amino-9-ethylcarbazol (AEC), 4-Chloro-1-naphthol (4-CN), Naphthol AS-TR phosphate, 5-bromo-4-chloro-3-indolyl phosphate (BCIP) or p-nitrophenylphosphate (pNPP).

Disclosed embodiments of a method for chromogenic detection of two or more molecules in a single tissue sample also may include contacting the tissue sample with a second, hapten-labeled specific binding moiety that specifically binds a second target molecule. In some embodiments, a hapten of the second, hapten-labeled specific binding moiety is an electron-deficient aromatic compound.

Disclosed embodiments of the method include treating the tissue sample with a solution containing a soluble electron-rich aromatic compound prior to or concomitantly with contacting the tissue sample with a second labeled specific binding moiety, such as a hapten-labeled specific binding moiety. In one example, treating the tissue sample with the solution containing a soluble, electron-rich aromatic compound occurs prior to contacting the tissue sample with the second, hapten-labeled specific binding moiety. In another example, treating the tissue sample with the solution containing a soluble electron-rich aromatic compound occurs concomitantly with contacting the second, hapten-labeled specific binding moiety with the tissue sample.

The disclosed embodiments for chromogenic detection of two or molecules also includes detecting the second target molecule by depositing a second, insoluble chromogen product that is distinguishable (such as visually distinguishable) from the insoluble, electron-rich aromatic compound deposited to detect the first target molecule. Treating the tissue sample with a solution containing the soluble, electron-rich aromatic compound reduces background due to non-specific binding of the hapten-labeled specific binding moiety to the insoluble, electron-rich compound deposited near the first target molecule. In a particular example, the soluble electron rich aromatic compound is naphthol.

For example, the second, hapten-labeled specific binding moiety may be a hapten-labeled nucleic acid probe, such as a hapten-labeled DNA probe (e.g., a DNP-labeled DNA probe). In some examples, the concentration of the DNP nucleic acid-labeled probe is sufficient to prevent or reduce background staining due to the DNP-labeled nucleic acid probe binding non-specifically to a chromogen product associated with a first target molecule. In certain examples, the concentration of DNP-labeled probe is greater than 1 and typically at least 5 µg/ml. For example, the concentration of the DNP nucleic acid-labeled probe ranges from 10 µg/ml to 15 µg/ml.

In an example, the first target molecule is a protein and the second target molecule is a nucleic acid sequence that encodes the first target molecule protein. The first target molecule and second target molecule can be associated with a disorder or disease, including cancer, such as a HER2 protein, c-Myc protein, n-Myc protein, Abl protein, EGFR protein, TOP2A protein, Bcl2 protein, Bcl6 protein, Rb1 protein, p53 protein, or c-Met protein or a nucleic acid that encodes one of these proteins. In one example, detecting the first target molecule includes performing immunohistochemistry (IHC) and detecting the second target molecule includes performing in situ hybridization (ISH). Performing IHC may comprise detecting the first target molecule by an enzyme-mediated system, such as an alkaline phosphatase red chromogen complex detection system or a horseradish peroxidase-DAB chromogen complex detection system. Performing ISH may comprise detecting the second target molecule by the same or different enzyme mediated system, such as a horseradish peroxidase silver staining ISH detection or an alkaline phosphatase red silver detection system. The method can be automated or manual.

In particular embodiments of the disclosed method, an automated nucleic acid/protein detection method is disclosed that allows dual nucleic acid/protein detection in the same tissue sample in a single automated run. One disclosed embodiment of the method includes automatically dispensing a primary antibody onto a tissue sample under conditions sufficient for the primary antibody to specifically bind a first target molecule within the tissue sample. This embodiment also includes detecting the first target molecule in the tissue sample with the primary antibody by IHC. This disclosed embodiment also includes automatically dispensing a hapten-labeled nucleic acid probe onto the tissue sample under conditions sufficient for such probe to specifically bind a second target molecule. In some examples, the hapten-labeled nucleic acid probe comprises an electron-deficient aromatic compound. The electron-deficient aromatic compound can have a formula as described above. This embodiment also can involve treating the tissue sample with a solution containing an electron-rich aromatic compound prior to or concomitantly with automatically dispensing the second, hapten-labeled nucleic acid probe onto the tissue sample and detecting the second target molecule by ISH. In such embodiments, the electron-rich aromatic compound can have a general formula as described herein. In a particular example, the electron-rich aromatic compound comprises naphthol. When Naphthol AS-TR phosphate (or Naphthol AS-MX phosphate, etc.) is utilized as the electron rich aromatic compound, the naphthol concentration may vary, but typically ranges from 1 to 60 milligrams per milliliter, such as between 25 milligrams per milliliter to 50 milligrams per milliliter, such as between 10 milligrams per milliliter to 40 milligrams per milliliter. In some particular examples, the naphthol concentration is about 50 milligrams per milliliter or about 25 milligrams per milliliter. When Naphthalen-1-ol or Naphthalen-2-ol, for example, are utilized as the electron rich aromatic compound, the naphthol concentration may vary, such as between 0.2 milligrams per milliliter to 7 milligrams per milliliter, such as 0.3 milligrams per milliliter to 1 milligram per milliliter.

In one embodiment of this method, automatically dispensing the hapten-labeled nucleic acid probe onto the tissue sample occurs after treating the tissue sample with an electron rich aromatic compound. In another embodiment, automatically dispensing the hapten-labeled nucleic acid probe onto the tissue sample occurs simultaneously with treating the tissue sample with an electron rich aromatic compound, in which the electron rich aromatic compound and nucleic acid labeled probe are provided to the tissue sample either substantially simultaneously or in the same solution. In some examples, the hapten-labeled nucleic acid probe is a hapten-labeled DNA probe, such as a DNP-labeled DNA probe.

In some embodiments of the method, IHC is performed prior to ISH. In other embodiments, ISH is performed prior to IHC. In some examples, ISH includes detecting the targeted nucleic acid by a horseradish peroxidase silver staining detection system or an alkaline phosphatase Fast Red/Naphthol phosphate staining detection system. In some examples, IHC detection includes detecting the targeted protein by an alkaline phosphatase Fast Red/Naphthol phosphate chromogen detection system or a horseradish peroxidase-DAB chromogen detection system.

Kits for performing the disclosed embodiments of the method are also provided. The embodiments of the method and kits disclosed herein can be used to detect targets in samples from mammals that are suspected of having a disorder or disease, such as cancer.

In a particular embodiment, a method for chromogenic detection of two or more target molecules in a single tissue sample comprises: contacting the tissue sample with a first specific binding moiety that specifically binds a first target molecule; detecting the first target molecule in the tissue sample by depositing an insoluble, electron-rich aromatic chromogen product; contacting the tissue sample with a second, hapten-labeled specific binding moiety that specifically binds a second target molecule, where a hapten of the second, hapten-labeled specific binding moiety comprises an electron-deficient aromatic compound; treating the tissue sample with a solution comprising a soluble, electron-rich aromatic compound prior to or concomitantly with contacting the second, hapten-labeled specific binding moiety with the tissue sample; and detecting the second target molecule by depositing a second, insoluble chromogen product that is distinguishable from the insoluble, electron-rich aromatic compound deposited to detect the first target molecule, where treating the tissue sample with the solution containing the soluble, electron-rich aromatic compound reduces background due to non-specific binding of the hapten-labeled specific binding moiety to the insoluble electron rich compound deposited near the first target molecule.

In one embodiment of the method the soluble, electron-rich aromatic compound has the formula

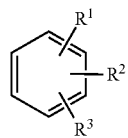

where at least one of $R^1$, $R^2$, $R^3$ are electron donating groups, independently selected from —$OR^4$, —$NR^6R^7$, —$OPO_3^{2-}$ and where $R^6$ and $R^7$ independently are H or lower alkyl or two of $R^1$, $R^2$ and $R^3$ together form a fused aromatic ring, optionally substituted with one, two or three electron donating substituents.

In one embodiment of the method, $R^2$ and $R^3$ together form a fused aromatic ring, the electron rich aromatic compound having the formula

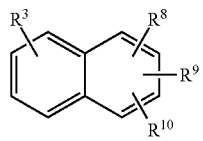

where $R^8$, $R^9$ and $R^{10}$ independently are selected from H, $-OR^{11}$, $-NR^{12}R^{13}$, $-OPO_3^{2-}$ or lower alkyl; and $R^{11}$, $R^{12}$ and $R^{13}$ independently are selected from H and lower alkyl.

In one embodiment of the method, the soluble, electron-rich aromatic compound comprises naphthol, and where the naphthol concentration reduces background due to non-specific binding of the hapten-labeled specific binding moiety to the insoluble, electron-rich compound deposited near the first target molecule and ranges from 1 milligrams per milliliter to 30 milligrams per milliliter, from about 1 milligrams per milliliter to about 7 milligrams per milliliter, from about 0.3 milligrams per milliliter to about 1 milligrams per milliliter or from about 0.3 milligrams per milliliter to about 1 milligrams per milliliter. For example, the second, hapten-labeled specific binding moiety is a hapten-labeled nucleic acid probe, such as where the hapten-labeled nucleic acid probe is a DNA probe. In an embodiment, the hapten of the hapten-labeled nucleic acid probe is a nitroaryl compound, such as dinitrophenol. In one embodiment, the method comprises a hapten-labeled nucleic acid probe that is dinitrophenol and the concentration of the dinitrophenol nucleic acid-labeled probe is at least 5 μg/ml, such as from 10 μg/ml to 15 μg/ml.

In one embodiment of the method, the hapten of the second, hapten-labeled probe is a nitroaryl compound, such as dinitrophenol.

In one embodiment of the method, the first target molecule is a protein and the second target molecule is a nucleic acid sequence, such as a nucleic acid sequence that encodes the first target molecule protein. For example, the protein is HER2/neu, c-Myc, n-Myc, Abl, EGFR protein, TOP2A, Bcl2, Bcl6, Rb1, p53, or c-Met and the nucleic acid sequence is a nucleic acid sequence encoding HER2, c-Myc, n-Myc, Abl, EGFR, TOP2A, Bcl2, Bcl6, Rb1, p53, c-Met.

In one embodiment of the method, the first target molecule and second target molecule are a first protein and a second protein.

In one embodiment of the method, the first target molecule and second target molecule are a first nucleic acid sequence and a second nucleic acid sequence.

In some embodiments of the method, treating the tissue sample with the solution containing a soluble, electron-rich aromatic compound comprises treating the tissue sample with the solution containing a soluble, electron-rich aromatic compound prior to contacting the second, hapten-labeled specific binding moiety with the tissue sample.

In some embodiments of the method, treating the tissue sample with the solution containing a soluble, electron-rich aromatic compound comprises treating the tissue sample with the solution containing a soluble, electron-rich aromatic compound concomitantly with contacting the second, hapten-labeled specific binding moiety with the tissue sample.

In one embodiment of the method, the first specific binding moiety is a primary antibody, such as a primary antibody that binds to HER2, c-Myc, n-Myc, Abl, EGFR protein, C-Met, TOP2A, Bcl2, Bcl6, Rb1, p53, or c-MET peptides.

In one embodiment of the method, the insoluble, electron-rich aromatic compound comprises an azo dye.

In one embodiment of the method, chromogenically depositing comprises reacting a substrate with a catalyst to directly or indirectly form the insoluble, electron-rich aromatic compound. For example, the catalyst is an enzyme, such as alkaline phosphatase or horseradish peroxidase. In one embodiment, the substrate is 3,3'-Diaminobenzidine (DAB), 3-Amino-9-ethylcarbazol (AEC), 4-Chloro-1-naphthol (4-CN), Naphthol AS-TR phosphate, 5-Bromo-4-chloro-3-indolyl phosphate (BCIP) or Nitrophenylphosphate (pNPP).

In one embodiment, detecting the first target molecule comprises performing immunohistochemistry (IHC) and detecting the second target molecule comprises performing in situ hybridization (ISH) in which performing IHC comprises detecting the first target molecule by an alkaline phosphatase-red chromogen detection system or a horseradish peroxidase-DAB chromogen detection system and performing ISH comprises detecting the second target molecule by a horseradish peroxidase silver ISH detection or an alkaline phosphatase red silver detection system.

In one embodiment, the method is performed by automation.

In one embodiment of the method, an automated nucleic acid and protein detection method is provided comprising: automatically dispensing a primary antibody onto a tissue sample under conditions sufficient for the primary antibody to specifically bind a first target molecule within the tissue sample; detecting the first target molecule in the tissue sample with the primary antibody by IHC; automatically dispensing a hapten-labeled nucleic acid probe onto the tissue sample under conditions sufficient for the hapten-labeled nucleic acid probe to specifically bind a second target molecule, where the hapten-labeled nucleic acid probe comprises an electron-deficient aromatic compound; treating the tissue sample with a solution containing an electron-rich aromatic compound prior to or concomitantly with automatically dispensing the second, hapten-labeled nucleic acid probe onto the tissue sample; and detecting the second target molecule by in situ hybridization (ISH), thereby allowing dual nucleic acid and protein detection in the same tissue sample in a single automated run, where the electron-rich aromatic compound has the formula

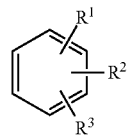

where at least one of $R^1$, $R^2$, $R^3$ are electron donating groups, independently selected from $-OR^4$, $-NR^6R^7$, where $R^6$ and $R^7$ independently are H or lower alkyl or two of $R^1$, $R^2$ and $R^3$ together form a fused aromatic ring, optionally substituted with one, two or three electron donating substituents.

In one embodiment of the automated nucleic acid and protein detection method, the electron-rich aromatic compound in which R2 and R3 together form a fused aromatic ring, the electron rich aromatic compound having the formula

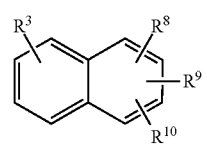

where R8, R9 and R10 independently are selected from H, $-OR^{11}$, $-NR^{12}R^{13}$, or lower alkyl; and $R^{11}$, $R^{12}$ and $R^{13}$ independently are selected from H and lower alkyl.

In one embodiment of the automated nucleic acid and protein detection method the electron-rich aromatic compound comprises naphthol, where the naphthol concentration is effective to allow dual nucleic acid and protein detection in a single sample and ranges from 1 milligrams per milliliter to 30 milligrams per milliliter, such as from 1 milligrams per milliliter to 7 milligrams per milliliter or from about 0.3 milligrams per milliliter to about 1 milligram per milliliter.

In one embodiment of the automated nucleic acid and protein detection method, the hapten of the hapten-labeled nucleic acid probe is a nitroaryl compound, such as where the nitroaryl compound is dinitrophenol. In one embodiment, the concentration of the dinitrophenol nucleic acid-labeled probe is at least 5 µg/ml, such as ranges from 10 µg/ml to 15 µg/ml.

In one embodiment of the automated nucleic acid and protein detection method, automatically dispensing a hapten-labeled nucleic acid probe onto the tissue sample under conditions sufficient for the hapten-labeled nucleic acid probe to specifically bind a second target molecule, occurs after treating the tissue sample with an electron-rich aromatic compound.

In one embodiment of the automated nucleic acid and protein detection method, automatically dispensing a hapten-labeled nucleic acid probe onto the tissue sample under conditions sufficient for the hapten-labeled nucleic acid probe to specifically bind a second target molecule, occurs simultaneously with treating the tissue sample with an electron-rich aromatic compound.

In one embodiment of the automated nucleic acid and protein detection method IHC is performed prior to ISH.

In one embodiment of the automated nucleic acid and protein detection method, ISH is performed prior to IHC.

In one embodiment of the automated nucleic acid and protein detection method, ISH comprises detecting the targeted nucleic acid by horseradish peroxidase-silver staining ISH or alkaline phosphatase-red silver staining.

In one embodiment of the automated nucleic acid and protein detection method, IHC comprises detecting the targeted protein by an alkaline phosphatase-red chromogen or a horseradish peroxidase-DAB chromogen.

In one embodiment, a kit for chromogenic detection of two or more target molecules in a single tissue sample comprises a solution containing a first specific binding moiety that specifically binds to a first target molecule; a solution containing a second, hapten-labeled specific binding moiety that specifically binds a second target molecule; a solution containing a soluble, electron-rich aromatic compound.

In one embodiment of the kit, the soluble, electron-rich aromatic compound is naphthol and the second, hapten-labeled specific binding moiety is a DNP-labeled nucleic acid probe.

In one embodiment of the kit, the solution containing the soluble, electron-rich aromatic compound further comprises the hapten-labeled nucleic acid probe.

The foregoing and other features of the disclosure will become more apparent from the following detailed description, which proceeds with reference to the accompanying colored figures.

µg/mL) allowing both EGFR protein and correlated nucleic acid sequences to be visualized with minimal background staining.

Figure 13:
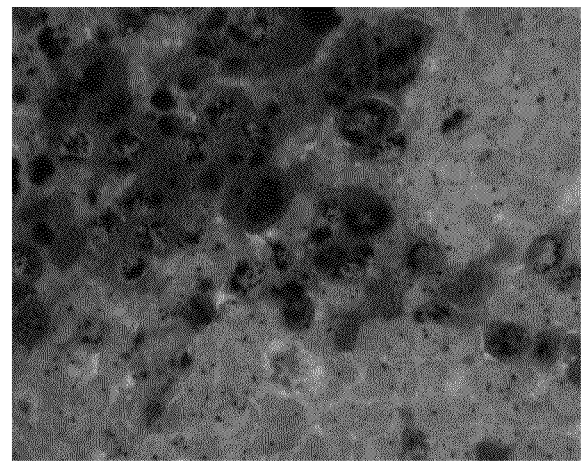

FIG. 13 is an exemplary microscopic (60×) view of a test sample (amplified) after IHC/ISH staining with a c-Met antibody (red) and c-Met probe (silver), in which the c-Met probe hybridization solution contained naphthol (300 µg/mL) allowing both c-Met protein and correlated nucleic acid sequences to be visualized with minimal background staining.

Figure 14:
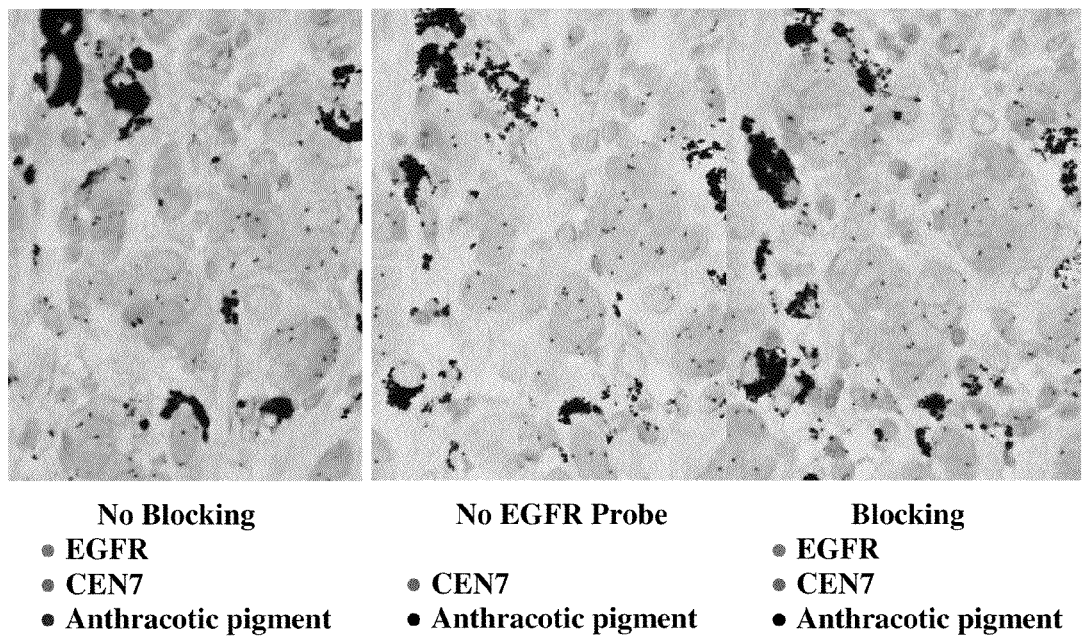

FIG. 14 is a series of microscopic views of test samples illustrating naphthol blockade of anthracotic pigments binding to DNP-labeled nick-translated DNA probes. The left panel illustrates dual color in situ hybridization for EGFR and chromosome 7 centromeric (CEN7) DNA probes. The enhanced appearance of the anthracotic pigments is seen as dark blue clusters (left panel). When the DNP-labeled nick translated probe was omitted from the assay (middle panel), the anthracotic pigments were seen as black clusters (the natural appearance of anthracotic pigments). When naphthol was added into the hybridization step with the EGFR DNP-labeled nick-translated probes (right panel) anthracotic pigments were seen as black clusters.

Figure 15:
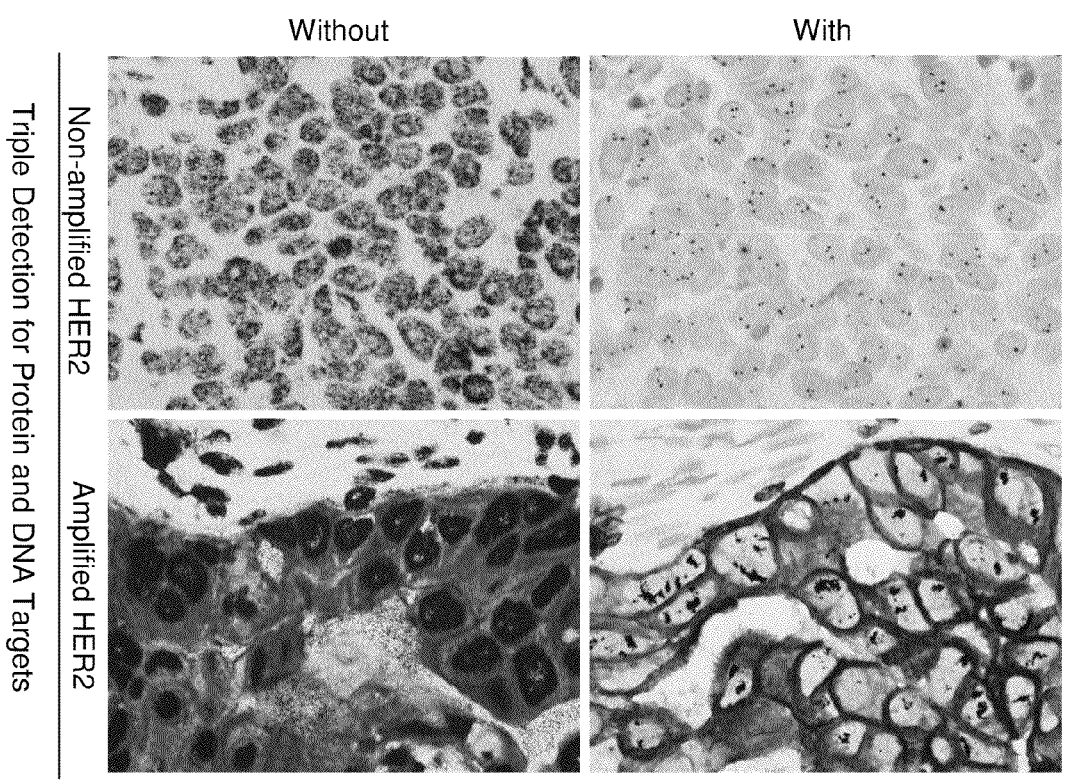

FIG. 15 is a series of microscopic views of test samples (non-amplified, top row; amplified, bottom row) treated with (left column) or without (right column) naphthol (25 mg/ml) in the hybridization buffer. The pictures illustrate that the chemical interaction between DAB and DNP and thus, background staining generated from the SISH detection, is eliminated by the naphthol treatment.

DETAILED DESCRIPTION OF THE INVENTION

I. Introduction

Diseases, such as cancer, can be diagnosed by a number of different methods. One method is to identify the presence of a biomarker, such as a cancer biomarker, in tissue or cells, the biomarker being correlated, or thought to be correlated, with a particular cancer type. Immunohistochemistry is oftentimes used to target protein biomarkers that are associated with a particular type of cancer, whereas in situ hybridization techniques are oftentimes employed to target nucleic acid sequences that are associated with a particular type of cancer.

Immunohistochemistry and in situ hybridization methods for target identification are becoming increasingly more important in research applications and for clinicians, for example for diagnostic and/or prognostic purposes. Current methods typically provide for the identification of one target, be it a protein or a nucleic acid sequence, per tissue or cell sample. However, it would be advantageous if an investigator could identify two or more targets on one tissue sample, for example identification of two or more different proteins, two or more different proteins and nucleic acid sequences, or two or more different nucleic acid sequences, thereby saving time, reagents and valuable tissue or cell samples. Such multiplexing of target identification would provide clinicians with the ability to more accurately diagnose diseases and provide more enlightened prognostic conclusions. The methods as described herein also find utility for companion diagnostics, where results provided by the disclosed methods are used not only for diagnosis, but also for determining the optimal treatment, and tracking the progression and success of such treatment, in a clinical setting.

The present invention provides for detection of two or more target molecules in a single tissue sample. In particular, to the present invention provides methods for chromogenically detecting two or more of a nucleic acid sequence and a protein, two proteins, or two nucleic acid sequences in the same tissue sample.

In developing embodiments of the present invention, it was noted that IHC experiments using a Fast Red/Naphthol phosphate complex detection system followed by ISH using a silver, HRP based, detection system resulted in a significant amount of silver background that impaired the ability to view the appropriate signal on the slide. A negative control slide experiment with no DNP-labeled nucleic acid probe showed no background, indicating that background was not due to the IHC reagents or the multimer-HRP conjugate. Subsequent studies suggested that background due to the Fast Red or the Fast Red/Naphthol phosphate complex was in large part due to interactions with the DNP-labeled DNA probe. No background was observed with the Rabbit anti-DNP antibody or the goat anti-rabbit-HRP conjugate system components.

To determine which system component was responsible for the background, various components of the ISH system were substituted out of the system. The presence of the DNP-labeled DNA probe was important for the background to be present. If the background was due to the multimer-HRP conjugate then it was contemplated that background would be present when just the DNP-labeled DNA probe was removed from the system, however this was not the case. Further evidence demonstrating that background was caused by the DNP-labeled probe was obtained when the background was eliminated upon Naphthol AS-TR phosphate addition and co-incubation with the DNP-labeled probe on the slide. The presence of naphthol blocked the DNP-labeled probe from binding to the Fast Red/Naphthol phosphate complex, thus decreasing the background.

The silver background was not always reproducible and it varied from instrument to instrument and from run to run making it difficult to trace to either instrument or reagent related causes. Although silver background was observed with various DNP-labeled probes, background was not observed with an FITC-labeled probe. These studies suggested that the silver background was a result of the DNP molecule interacting with the Fast Red chromogen. This was confirmed by performing studies in which free DNP was incubated with tissue after the Fast Red chromogen development. The results from this study resulted in comparable silver background associated with the Fast Red chromogen pattern.

In developing embodiments of the present invention, experiments were undertaken to identify compounds and procedures that could be utilized to inhibit or reduce the observed non-specific background. A series of studies were performed that upon conclusion indicated that the DNP portion of the DNP-labeled probes was binding primarily to the naphthol phosphate component of the Fast Red/Naphthol phosphate complex. Although the exact nature of the DNP interaction with the naphthol phosphate component on the slide is unknown, it is contemplated that the observed non-specific binding is due to the binding of an electron-deficient aromatic compound (in this case the DNP hapten) to an electron-rich chromogen complex (e.g., a Fast Red/Naphthol phosphate complex), such as by pi stacking.

Based on these observations, the present disclosure is particularly directed to a process and/or composition that provides dual detection by substantially reducing or preventing non-specific binding of an electron-deficient aromatic compound (such as a hapten) to an electron-rich chromogen complex during chromogenic-detection of two or more target molecules in a single sample. Certain disclosed embodiments concern processes and/or compositions that substantially reduce or prevent pi stacking of an electron-deficient aromatic compound to the electron-rich chromogen complex. The method may be automated or performed manually.

II. Abbreviations and Terms

Unless otherwise noted, technical terms are used according to conventional usage. Definitions of common terms in molecular biology may be found in Benjamin Lewin, Genes VII, published by Oxford University Press, 2000; Kendrew et al. (eds.), The Encyclopedia of Molecular Biology, published by Blackwell Publishers, 1994); Robert A. Meyers (ed.), Molecular Biology and Biotechnology: a Comprehensive Desk Reference, published by Wiley, John & Sons, Inc., 1995; and George P. Rédei, Encyclopedic Dictionary of Genetics, Genomics, and Proteomics, 2nd Edition, 2003.

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise.

Although methods and materials similar or equivalent to those described herein can be used to practice or test the disclosed technology, suitable methods and materials are described below. The materials, methods, and examples are illustrative only and not intended to be limiting.

To facilitate review of the various embodiments of this disclosure, the following explanations of specific terms are provided:

Alkaline phosphatase: A hydrolase enzyme that removes phosphate $(P(O)(OR)_3)$ groups from a molecule. For example, alkaline phosphatase hydrolyzes naphthol phosphate esters (substrate) to phenolic compounds and phosphates. The phenols azo couple to colorless diazonium salts (chromogen such as Fast Red) producing an insoluble, colored precipitate.

Aliphatic: Moieties including alkyl, alkenyl, alkynyl, halogenated alkyl and cycloalkyl groups as described below. A "lower aliphatic" group is a branched or unbranched aliphatic group having from 1 to 10 carbon atoms.

Alkyl: A branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. The terms "halogenated alkyl" or "haloalkyl group" refer to an alkyl group as defined above with one or more hydrogen atoms present on these groups substituted with a halogen (F, Cl, Br, I). The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulfur, or phosphorous. Optionally substituted groups, such as "substituted alkyl," describes groups, such as an alkyl group, having from 1-5 substituents, typically from 1-3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, optionally substituted heteroaryl, optionally substituted heterocyclyl, hydroxy, thiol and thioalkoxy.

Antibody: A polypeptide that includes at least a light chain or heavy chain immunoglobulin variable region and specifically binds an epitope of an antigen. Antibodies include monoclonal antibodies, polyclonal antibodies, or fragments of antibodies as well as others known in the art. In some examples, an antibody is labeled with a detectable label, such as an enzyme or fluorophore.

Antigen: A molecule that stimulates an immune response. Antigens are usually proteins or polysaccharides. An epitope is an antigenic determinant composed of chemical groups or peptide sequences on a molecule that elicit a specific immune response. An antibody binds a particular antigen or epitope. The binding of an antibody to a particular antigen or epitope of an antigen can be used to localize the position of the antigen for example in or on a biological sample, or determine if the particular antigen is present in a biological sample. An antigen of interest is an antigen an IHC assay is designed to detect in a test sample. For example, to detect an antigen of interest, the primary antibody used in the IHC assay specifically binds to the antigen of interest.

Binding or stable binding: An association between two substances or molecules, such as the association of a specific binding agent (e.g., antibody) with an antigen.

Chromogen: A substance capable of conversion to a colored product, such as a pigment or dye. Certain chromogens are electron donors that, when oxidized, become a colored product. Production of a colored product, and the property of becoming insoluble upon chemical conversion, such as by oxidation, make chromogens useful for IHC. Particular examples of chromogenic compounds, without limitation, include diaminobenzidine (DAB), 4-Chloro-2-methyl-benzenediazonium (Fast Red), nitro blue tetrazolium (NBT), AP Orange, tetramethylbenzidine (TMB), 2,2'-azino-di-[3-ethylbenzothiazoline sulphonate] (ABTS), New Fuchsin, iodonitrotetrazolium (INT), tetrazolium blue and tetrazolium violet.

DAB is a chromogen that produces a brown end product that is highly insoluble in alcohol and other organic solvents. Oxidation of DAB causes polymerization, resulting in the ability to react with osmium tetroxide, and thus increasing its staining intensity and electron density. Of the several metals and methods used to intensify the optical density of polymerized DAB, gold chloride in combination with silver sulfide appears to be the most successful.

Diazonium salts are additional examples of chromogens that couple to phenols produced by the enzyme alkaline phosphatase by, for example, hydrolyzing naphthol phosphate esters (substrate) to phenolic compounds and phosphates. The chromogens Fast Red TR and Fast Blue BB produce a bright red or blue end product, respectively. Both are soluble in alcoholic and other organic solvents, so aqueous mounting media is used. New Fuchsin also gives a red end product. Unlike Fast Red TR and Fast Blue BB, the color produced by New Fuchsin is insoluble in alcohol and other organic solvents, allowing specimens to be dehydrated before coverslipping.

Conditions sufficient to detect: Any environment that permits the desired activity, for example, that permits a probe to bind a target and the interaction to be detected. For example, such conditions include appropriate temperatures, buffer solutions, and detection means such as microscopes and digital imaging equipment.

Contacting: Placement that allows association between two or more moieties, particularly direct physical association, for example both in solid form and/or in liquid form (for example, the placement of a biological sample, such as a biological sample affixed to a slide, in contact with an antigen releasing solution).

Control: A sample or procedure performed to assess test validity. In one example, a control is a quality control, such as a positive control. For example, a positive control is a procedure or sample, such as a tissue or cell, that is similar to the actual test sample, but which is known from previous experience to give a positive result. The positive control confirms that the basic conditions of the test produce a positive result, even if none of the actual test samples produce such result. In a particular example, a positive control is a sample known by previous testing to contain the suspected antigen.

In other examples, a control is a negative control. A negative control is a procedure or test sample known from previous experience to give a negative result. The negative control demonstrates the base-line result obtained when a test does not produce a measurable positive result; often the value of the negative control is treated as a "background" value to be subtracted from the test sample results. In a particular example, a negative control is a reagent that does not include the specific primary antibody. Other examples include calibrator controls, which are samples that contain a known amount of a control antigen. Such calibrator controls have an expected signal intensity, and therefore can be used to correct for inter- or intra-run staining variability.

Detect: To determine if an agent (such as a signal or particular antigen or protein) is present or absent, for example, in a sample. In some examples, this can further include quantification. "Detecting" refers to any method of determining if something exists, or does not exist, such as determining if a target molecule is present in a biological sample. For example, "detecting" can include using a visual or a mechanical device to determine if a sample displays a specific characteristic. In certain examples, detection refers to visually observing a probe bound to a target, or observing that a probe does not bind to a target. For example, light microscopy and other microscopic means are commonly used to detect chromogenic precipitates for methods described here.

Detectable Label: A molecule or material that can produce a detectable (such as visually, electronically or otherwise) signal that indicates the presence and/or concentration of a target in a sample. When conjugated to a specific binding molecule, the detectable label can be used to locate and/or quantify the target to which the specific binding molecule is directed. Thereby, the presence and/or concentration of the target in a sample can be detected by detecting the signal produced by the detectable label. A detectable label can be detected directly or indirectly, and several different detectable labels conjugated to different specific-binding molecules can be used in combination to detect one or more targets. For example, a first detectable label, such as a hapten conjugated to an antibody specific to a target, can be detected indirectly by using a second detectable label that is conjugated to a molecule that specifically binds the first detectable label. Multiple detectable labels that can be separately detected can be conjugated to different specific binding molecules that specifically bind different targets to provide a multiplexed assay that can provide detection of the multiple targets in a sample.

Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Particular examples of detectable labels include: enzymes, such as horseradish peroxidase, alkaline phosphatase, acid phosphatase, glucose oxidase, β-galactosidase or β-glucuronidase; fluorphores, such as fluoresceins, luminophores, coumarins, BODIPY dyes, resorufins, and rhodamines (many additional examples of fluorescent molecules can be found in The Handbook—A Guide to Fluorescent Probes and Labeling Technologies, Molecular Probes, Eugene, Oreg.); nanoparticles, such as quantum dots (U.S. Pat. Nos. 6,815,064, 6,682596 and 6,649,138, each of which patents is incorporated by reference herein); metal chelates, such as DOTA and DPTA chelates of radioactive or paramagnetic metal ions like $Gd^{3+}$; and liposomes, for example, liposomes containing trapped fluorescent molecules. Where the detectable label includes an enzyme, a detectable substrate such as a chromogen, a fluorogenic compound, or a luminogenic compound is used in combination with the enzyme to generate a detectable signal (a wide variety of such compounds are commercially available, for example, from Life Technologies, Carlsbad, Calif.).

Alternatively, an enzyme can be used in a metallographic detection scheme. Metallographic detection methods include using an enzyme, such as alkaline phosphatase, in combination with a water-soluble metal ion and a redox-inactive substrate of the enzyme. The substrate is converted to a redox-active agent by the enzyme, and the redox-active agent reduces the metal ion, causing it to form a detectable precipitate. (See, for example, co-pending U.S. patent application Ser. No. 11/015,646, filed Dec. 20, 2004, PCT Publication No. 2005/003777 and U.S. Patent Application Publication No. 2004/0265922; each of which is incorporated by reference herein). Metallographic detection methods include using an oxido-reductase enzyme (such as horseradish peroxidase) along with a water soluble metal ion, an oxidizing agent and a reducing agent, again to form a detectable precipitate. (See, for example, U.S. Pat. No. 6,670,113, which is incorporated by reference herein). Haptens are small molecules that are bound by antibodies, although by themselves they will not elicit an immune response in an animal and must first be attached to a larger carrier molecule, such as a protein, to generate an immune response. Examples of haptens include dinitrophenyl, biotin, digoxigenin, and fluorescein. Additional examples including oxazole, pyrazole, thiazole, nitroaryl, benzofuran, triperpene, urea, thiourea, rotenoid, coumarin and cyclolignan haptens are disclosed in co-pending U.S. patent application Ser. No. 11/982,627, filed Nov. 1, 2007, which is incorporated by reference herein.

Electron-deficient: Indicates a pi-system, such as an alkene or arene, that has electron-withdrawing groups attached, as found in nitrobenzene or acrylonitrile. Instead of exhibiting the typical reactivity common to such moities, the electron-deficient pi-systems may be electrophilic and susceptible to nucleophilic attack. In an example, an electron deficient hapten is DNP.

Epitope: A site on a target molecule (e.g., an antigen, such as a protein or nucleic acid molecule) to which an antigen binding molecule (e.g., an antibody, antibody fragment, scaffold protein containing antibody binding regions, or aptamer) binds. Epitopes can be formed both from contiguous or juxtaposed noncontiguous residues (e.g., amino acids or nucleotides) of the target molecule (e.g., a protein-protein interface). Epitopes formed from contiguous residues (e.g., amino acids or nucleotides) typically are retained on exposure to denaturing solvents whereas epitopes formed by tertiary folding typically are lost on treatment with denaturing solvents. An epitope typically includes at least 3, and more usually, at least 5 or 8 10 residues (e.g., amino acids or nucleotides). Typically, an epitope also is less than 20 residues (e.g., amino acids or nucleotides) in length, such as less than 15 residues or less than 12 residues.

Fixation: A process which preserves cells and tissue constituents in as close to a life-like state as possible and allows them to undergo preparative procedures without change. Fixation arrests the autolysis and bacterial decomposition processes that begin upon cell death, and stabilizes the cellular and tissue constituents so that they withstand the subsequent stages of tissue processing, such as for IHC.

Tissues may be fixed by either perfusion with or submersion in a fixative, such as an aldehyde (such as formaldehyde, paraformaldehyde, glutaraldehyde, and the like). Other fixatives include oxidizing agents (for example, metallic ions and complexes, such as osmium tetroxide and chromic acid), protein-denaturing agents (for example, acetic acid, methanol, and ethanol), fixatives of unknown mechanism (for example, mercuric chloride, acetone, and picric acid), combination reagents (for example, Carnoy's fixative, methacarn, Bouin's fluid, B5 fixative, Rossman's fluid, and Gendre's fluid), microwaves, and miscellaneous (for example, excluded volume fixation and vapour fixation). Additives also may be included in the fixative, such as buffers, detergents, tannic acid, phenol, metal salts (for example, zinc chloride, zinc sulfate, and lithium salts), and lanthanum.

The most commonly used fixative in preparing samples for IHC is formaldehyde, generally in the form of a formalin solution (4% formaldehyde in a buffer solution, referred to as 10% buffered formalin).

Hapten: A molecule, typically a small molecule that can combine specifically with an antibody, but typically is substantially incapable of being immunogenic except in combination with a carrier molecule. Examples of haptens include, but are not limited to fluorescein, biotin, nitroaryls, including, but, not limited to, dinitrophenol (DNP), and digoxigenin.

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11).

Immunohistochemistry (IHC): A method of determining the presence or distribution of an antigen in a sample by detecting interaction of the antigen with a specific binding agent, such as an antibody. A sample including an antigen (such as a target antigen) is incubated with an antibody under conditions permitting antibody-antigen binding. Antibody-antigen binding can be detected by means of a detectable label conjugated to the antibody (direct detection) or by means of a detectable label conjugated to a secondary antibody, which is raised against the primary antibody (e.g., indirect detection). Detectable labels include, but are not limited to, radioactive isotopes, fluorochromes (such as fluorescein, fluorescein isothiocyanate, and rhodamine), and chromogenic molecules.

In situ hybridization (ISH): A type of hybridization that uses a labeled complementary DNA or RNA strand (i.e., probe) to localize a specific DNA or RNA sequence in a portion or section of tissue (in situ), or, if the tissue is small enough (e.g., plant seeds, *Drosophila* embryos), in the entire tissue (whole mount ISH). This is distinct from immunohistochemistry, which localizes proteins in tissue sections. DNA ISH can be used to determine the structure of chromosomes, such as for use in medical diagnostics to assess chromosomal integrity. RNA ISH (hybridization histochemistry) is used to measure and localize mRNAs and other transcripts within tissue sections or whole mounts.

For hybridization histochemistry, sample cells and tissues are usually treated to fix the target transcripts in place and to increase access of the probe to the target molecule. As noted above, the probe is either a labeled complementary DNA or a complementary RNA (Riboprobe). The probe hybridizes to the target sequence at elevated temperature, and then the excess probe is washed away (after prior hydrolysis using RNase in the case of unhybridized, excess RNA probe). Solution parameters, such as temperature, salt and/or detergent concentration, can be manipulated to remove any non-identical interactions (i.e. only exact sequence matches will remain bound). Then, the labeled probe having been labeled effectively, such as with either radio-, fluorescent- or antigen-labeled bases (e.g., digoxigenin), is localized and potentially quantitated in the tissue using either autoradiography, fluorescence microscopy or immunohistochemistry, respectively. ISH can also use two or more probes, labeled with radioactivity or the other non-radioactive labels, such as hapten labels, and typically differentially labeled to simultaneously detect two or more transcripts Lower alkyl: A saturated branched or unbranched hydrocarbon having from 1 to 10 carbon atoms.

Mammal: This term includes both human and non-human mammals. Similarly, the term "subject" includes both human and veterinary subjects.

Molecule of Interest or Target: A molecule for which the presence, location and/or concentration is to be determined. Examples of molecules of interest include nucleic acid sequences and proteins tagged with haptens.

Naphthol: Naphthol, or naphthalene-1-ol and naphthalene-2-ol is either of two colorless crystalline solid isoforms with the formula $C_{10}H_7OH$ that are positional isomers differing by the location of the hydroxyl group on naphthalene.

α-Naphthol is naphthalen-1-ol with a formula

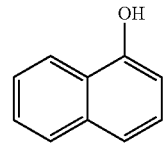 [SMILES: Oc1cccc2ccccc12]

β-naphthol is naphthalen-2-ol with a formula

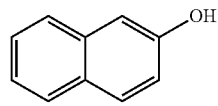 [SMILES: Oc1ccc2ccccc2c1]

Naphthol is the naphthalene homologue of phenol, with the hydroxyl group being more reactive than in the phenols. Naphthol is soluble in simple alcohols, ethers, and chloroform. In one example, naphthol is dissolved in hybridization buffer. Naphthol AS-TR phosphate, Naphthol AS-MX phosphate, etc. compounds are utilized as a substrate, for example by a phosphatase such as alkaline phosphatase, and are typical components of a Fast Red/Naphthol phosphate chromogen complex.

Neoplasia and Tumor: The process of abnormal and uncontrolled cell growth. Neoplasia is one example of a proliferative disorder.

The product of neoplasia is a neoplasm (a tumor), which is an abnormal growth of tissue that results from excessive cell division. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Nitroaryl: A general class of haptens that include, without limitation, nitrophenyl, nitrobiphenyl, nitrotriphenyl, etc., and any and all heteroaryl counterparts, having the following general chemical formula.

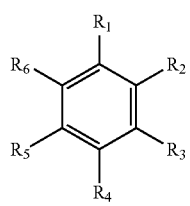

With reference to this general formula, such compounds have at least one, and optionally plural, nitro groups. Thus, at least one of $R_1$-$R_6$ is nitro. If more than one of $R_1$-$R_6$ is nitro, all combinations of relative ring positions of plural nitro substituents, or nitro substituents relative to other ring substituents, are included within this class of disclosed haptens. Dinitroaryl compounds are most typical. A person of ordinary skill in the art will appreciate that as the number of nitro groups increases, the number of remaining ring substituents in the general formula decreases. These substituents independently are selected from: hydrogen, acyl, aldehydes, alkoxy, aliphatic, particularly lower aliphatic, substituted aliphatic, heteroaliphatic, e.g., organic chains having heteroatoms, such as oxygen, nitrogen, sulfur, alkyl, particularly alkyl having 20 or fewer carbon atoms, and even more typically lower alkyl having 10 or fewer carbon atoms, such as methyl, ethyl, propyl, isopropyl, and butyl, substituted alkyl, such as alkyl halide (e.g., —$CX_3$ where X is a halide, and combinations thereof, either in the chain or bonded thereto), oxime, oxime ether (e.g., methoxyimine, $CH_3$—O—N=) alcohols (i.e. aliphatic or alkyl hydroxyl, particularly lower alkyl hydroxyl) amido, amino, amino acid, aryl, alkyl aryl, such as benzyl, carbohydrate, monosaccharides, such as glucose and fructose, disaccharides, such as sucrose and lactose, oligosaccharides and polysaccharides, carbonyl, carboxyl, carboxylate (including salts thereof, such as Group I metal or ammonium ion carboxylates), cyclic, heterocyclic, cyano (—CN), ester, ether, halogen, heteroaryl, hydroxyl, hydroxlyamine, oxime (HO—N=), keto, such as aliphatic ketones, nitro, sulfhydryl, sulfonyl, sulfoxide, exomethylene, and combinations thereof. At least one of the $R_1$-$R_6$ substituents is bonded to a linker or is a functional group suitable for coupling to a linker or a carrier molecule.

Two or more of the $R_1$-$R_6$ substituents also may be atoms, typically carbon atoms, in a ring system, such as napthalene (shown below) or anthracene type derivatives. Ring systems other than 6-membered ring systems can be formed, such as fused 6-5 ring systems.

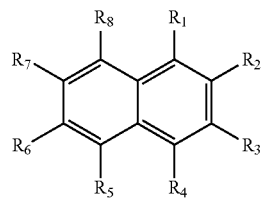

Again, at least one of the ring positions occupied by $R_1$-$R_8$ is bonded to a linker or is a variable functional group suitable for coupling, such as by covalent bonding, to a carrier molecule. For example, nitroaryl compounds can include a functional group for coupling to a carrier, or to a linker, at various optional ring locations.

Working embodiments are exemplified by nitrophenyl compounds. Solely by way of example, mononitroaryl compounds are exemplified by nitrocinnamide compounds. One embodiment of a nitrocinnamide-based compound is exemplified by 4,5-dimethoxy-2-nitrocinnamide, shown below.

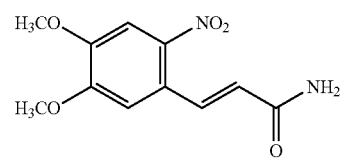 [SMILES: COc1cc(/C=C/C(N)=O)c([N+](=O)[O-])cc1OC]

The nitrophenyl class of compounds also is represented by dinitrophenyl compounds. At least one of the remaining carbon atoms of the ring positions not having a nitro group is bonded to a functional group, to a linker, or directly to a carrier. Any and all combinations of relative positions of these groups are included within the class of disclosed haptens.

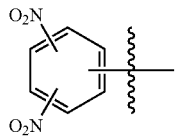

Working embodiments are more particularly exemplified by 2,4-dinitrophenyl compounds coupled to a linker, as illustrated below.

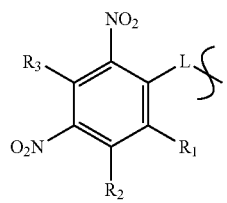

$R_1$-$R_3$ are as stated above.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15, or 20 bases.

Polymeric substance: A substance composed of molecules with large molecular mass composed of repeating structural units, or monomers, connected by covalent chemical bonds. As used herein, examples of polymeric substances can include paraffin, agarose, and gelatin.

Probe: An isolated nucleic acid, an isolated synthetic oligonucleotide, attached to a detectable label or reporter molecule. Typical labels include radioactive isotopes, enzyme substrates, co-factors, ligands, chemiluminescent or fluorescent agents, haptens (including, but not limited to, DNP), and enzymes. Methods for labeling and guidance in the choice of labels appropriate for various purposes are discussed, e.g., in Sambrook et al. (In Molecular Cloning: A Laboratory Manual, CSHL, New York, 1989) and Ausubel et al. (In Current Protocols in Molecular Biology, Greene Publ. Assoc. and Wiley-Intersciences, 1992).

One of ordinary skill in the art will appreciate that the specificity of a particular probe increases with its length. Thus, probes can be selected to provide a desired specificity, and may comprise at least 17, 20, 23, 25, 30, 35, 40, 45, 50 or more consecutive nucleotides of desired nucleotide sequence.

In particular examples, probes can be at least 100, 250, 500, 600 or 1000 consecutive nucleic acids of a desired nucleotide sequence.

Sample: The term "sample" refers to any liquid, semi-solid or solid substance (or material) in or on which a target can be present. In particular, a sample can be a biological sample or a sample obtained from a biological material. Examples of biological samples include tissue samples and cytology samples. In some examples, the biological sample is obtained from an animal subject, such as a human subject. A biological sample is any solid or fluid sample obtained from, excreted by or secreted by any living organism, including without limitation, single celled organisms, such as bacteria, yeast, protozoans, and amebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples, a biological sample is a nuclear extract. In some examples, a biological sample is bacterial cytoplasm. In certain examples, a sample is a quality control sample, such as one of the disclosed cell pellet section samples. In other examples, a sample is a test sample. For example, a test sample is a cell, a tissue or cell pellet section prepared from a biological sample obtained from a subject. In an example, the subject is one that is at risk or has acquired a particular condition or disease.

Specifically binds: A term that refers to the binding of agent that preferentially binds to a defined target (such as an antibody to a specific antigen or a nucleic acid probe to a specific nucleic acid sequence). With respect to an antigen, "specifically binds" refers to the preferential association of an antibody or other ligand, in whole or part, with a specific polypeptide With respect to a nucleic acid sequence, "specifically binds" refers to the preferential association of a nucleic acid probe, in whole or part, with a specific nucleic acid sequence A specific binding agent binds substantially only to a defined target. It is recognized that a minor degree of non-specific interaction may occur between a molecule, such as a specific binding agent, and a non-target polypeptide or non-target nucleic acid sequence. Although a selectively reactive antibody binds an antigen, it can do so with low affinity. Antibody to antigen specific binding typically results in greater than 2-fold, such as greater than 5-fold, greater than 10-fold, or greater than 100-fold increase in amount of bound antibody or other ligand (per unit time) to a target polypeptide, as compared to a non-target polypeptide. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

Nucleic acid probe to nucleic acid sequence specific binding typically results in greater than 2-fold, such as greater than 5-fold, greater than 10-fold, or greater than 100-fold increase in amount of bound nucleic acid probe to a target nucleic acid sequence, as compared to a non-target nucleic acid. A variety of ISH conditions are appropriate for selecting nucleic acid probes that bind specifically with a particular nucleic acid sequence (as described herein).

Specific Binding Moiety: A member of a specific-binding pair. Specific binding pairs are pairs of molecules that are characterized in that they bind each other to the substantial exclusion of binding to other molecules (for example, specific binding pairs can have a binding constant that is at least $10^3$ $M^{-1}$ greater, $10^4 M^{-1}$ greater or $10^5 M^{-1}$ greater than a binding constant for either of the two members of the binding pair with other molecules in a biological sample). Particular examples of specific binding moieties include specific binding proteins (for example, antibodies, lectins, avidins such as streptavidins, and protein A). Specific binding moieties can also include the molecules (or portions thereof) that are specifically bound by such specific binding proteins.

Substrate: A molecule acted upon by a catalyst, such as an enzyme. In one example, a substrate is 4-Chloro-1-naphthol (4-CN), Naphthol AS-TR phosphate, 5-Bromo-4-chloro-3-indolyl phosphate (BCIP), diaminobenzidine (DAB) or para-Nitrophenylphosphate (pNPP).

Target: Any molecule for which the presence, location and/or concentration is or can be determined. Examples of target molecules include proteins, nucleic acids and haptens, such as haptens covalently bonded to proteins or nucleic acid sequences. Target molecules are typically detected using one or more conjugates of a specific binding molecule and a detectable label.

Tissue: A collection of interconnected cells that perform a similar function within an organism.

III. Embodiments of a Method for Detection of Two or More Molecules in a Single Tissue Sample Disclosed embodiments comprise performing IHC or ISH on a sample in a manner that does not preclude performing a second IHC or ISH procedure. Thus, IHC-IHC, ISH-ISH, IHC-ISH or ISH-IHC procedures are performed. In a particular commercial embodiment, IHC and ISH are performed on the same sample.

Disclosed herein are embodiments comprising a method for chromogenic-detection of two or more target molecules in a single tissue sample. In one embodiment, the method comprises contacting the tissue sample with a first specific binding moiety that specifically binds a first target molecule. In one example, the first specific binding moiety is a primary antibody and the first target molecule is a protein. For example, the primary antibody is an antibody that detects a protein associated with cancer, such as a HER2, c-Myc, n-Myc, Abl, EGFR, TOP2A, Bcl2, Bcl6, Rb1, p53, or c-Met.

Some embodiments of the method comprise detecting a first target molecule in the tissue sample. For example, the first target molecule is detected chromogenically by adding a chromogen, such as an insoluble electron-rich aromatic compound, to the sample in such a manner as to detect the first specific binding moiety binding to the first target molecule. In one embodiment, the insoluble electron-rich aromatic compound is an azo dye. In some examples, depositing a chromogen comprises reacting a substrate with a catalyst to form the insoluble electron rich aromatic compound. For example, the catalyst is an enzyme, such as alkaline phosphatase or horseradish peroxidase. A substrate for the enzyme is selected, such as 3,3'-Diaminobenzidine (DAB), 3-Amino-9-ethylcarbazol (AEC), 4-Chloro-1-naphthol (4-CN), Naphthol AS-TR phosphate, 5-Bromo-4-chloro-3-indolyl phosphate (BCIP) or para-Nitrophenylphosphate (pNPP). In a particular embodiment, a DAB-based chromogenic detection system is employed. For example, a DAB-IHC detection system is utilized to detect a first protein target. In another embodiment, a Fast Red alkaline phosphatase detection system is employed. In one embodiment, a Fast Red alkaline phosphatase IHC detection system is employed to detect a first protein target. For example, the ULTRAVIEW RED Detection Kits as disclosed herein use an alkaline-phosphatase-labeled cocktail of antibodies to localize a bound primary antibody. The primary antibody, alkaline-phosphatase-labeled antibody complex is visualized using a Fast Red/Naphthol phosphate chromogen complex. A positive result provides a bright red precipitate localized at the site of binding. For example, when performing IHC on a dermatopathology tissue sample a bright red color provides differentiation between a target protein and naturally occurring melanin pigments in the sample.

In one embodiment, a method for chromogenic-detection of two or more targets in a single tissue sample comprises contacting the tissue sample with a second, hapten-labeled binding moiety that specifically binds a second target molecule. In some embodiments, the hapten of the second, hapten-labeled binding moiety is an electron-deficient aromatic compound. For example, the second, hapten-labeled specific binding moiety is a hapten-labeled nucleic acid probe, such as a hapten-labeled DNA probe (e.g., a DNP-labeled DNA probe). In some embodiments, the concentration of the DNP nucleic acid-labeled probe is at least 5 µg/ml. In some embodiments, the concentration of the DNP nucleic acid-labeled probe ranges from approximately 10 µg/ml to approximately 15 µg/ml.

In one embodiment, the first target molecule is a protein and the second target molecule is a protein. In another embodiment, the first target molecule is a protein and the second target molecule is a nucleic acid sequence. In other embodiments, the first target is a nucleic acid sequence and the second target molecule is a nucleic acid sequence. For example, the first target molecule is a protein and the second target molecule is a nucleic acid sequence that correlates with the target molecule protein (e.g., nucleic acid sequence that encodes the target protein, or nucleic acid sequences at or near the chromosomal location wherein the target protein encoding sequences are located). The first target molecule and second target molecule can be a molecule associated with cancer, such as a HER2 protein, c-Myc protein, n-Myc protein, Abl protein, EGFR protein, TOP2A protein, Bcl2 protein, Bcl6 protein, Rb1 protein, p53 protein, or c-Met protein or a nucleic acid that encodes one of these proteins, or nucleic acid sequences at or near the chromosomal location wherein the encoding sequences are located. In one example, detecting the first target molecule includes performing IHC and detecting the second target molecule includes performing ISH. Performing IHC comprises detecting the first target molecule by an alkaline phosphatase red chromogen detection system or a horseradish peroxidase-DAB chromogen detection system. Performing ISH comprises detecting the second target molecule by a horseradish peroxidase silver ISH detection or an alkaline phosphatase red silver detection system. The chromogenic detection methods can be performed by automation or manually.

Disclosed embodiments include treating the tissue sample with a solution containing a soluble electron-rich aromatic compound prior to, concomitantly with or substantially concomitantly with contacting the second, hapten-labeled specific binding moiety with the tissue sample. In one embodiment, treating the tissue sample with the solution comprising a soluble electron-rich aromatic compound occurs prior to contacting the second, hapten-labeled specific binding moiety with the sample. In another embodiment, treating the tissue sample with the solution comprising a soluble electron-rich aromatic compound occurs concomitantly, or at least substantially so, with contacting the second, hapten-labeled specific binding moiety with the sample.

The disclosed method for chromogenic detection of two or molecules further comprises detecting the second target molecule by depositing a second insoluble chromogen that is distinguishable from the insoluble, electron-rich aromatic compound used to detect the first target molecule. Treating a tissue sample with a solution comprising a soluble, electron-rich aromatic compound reduces background due to nonspecific binding of the hapten-labeled specific binding moiety to the insoluble, electron-rich compound deposited near the first target molecule.

In one embodiment, the soluble, electron-rich aromatic compound has the general formula

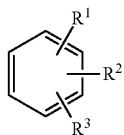

wherein at least one of the $R^1$, $R^2$ and $R^3$ are electron donating groups independently selected from; H, —$OR^4$, —$NR^6R^7$, —$OPO_3^{2-}$ and lower alkyl; two of $R^1$, $R^2$ and $R^3$ form a fused ring, or a ring having one or more sites unsaturated in conjunction with the first aromatic ring, optionally substituted with one, two or three electron donating substituents; and wherein $R^6$ and $R^7$ independently are H or a lower alkyl.

In a further embodiment, $R^2$ and $R^3$ together form a fused aromatic ring, the electron rich aromatic compound having the formula

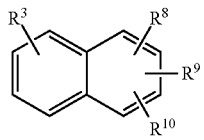

wherein $R^8$, $R^9$ and $R^{10}$ are independently selected from; H, —$OR^{11}$, —$NR^{12}R^{13}$, —$OPO_3^{2-}$ and lower alkyl, and $R^{11}$, $R^{12}$ and $R^{13}$ are independently selected from; H and lower alkyl. In a particular embodiment, the soluble electron rich aromatic compound is a hydroxy aryl or hydroxyl biaryl compound, such as naphthol.

In a particular embodiment of the disclosed method, an automated nucleic acid protein detection method is disclosed that provides dual nucleic acid/protein detection in the same tissue sample in a single automated run. One disclosed embodiment of the method comprises automatically dispensing a primary antibody onto a tissue sample under conditions sufficient for the primary antibody to specifically bind a first target molecule within the tissue sample. In some embodiments, methods as disclosed herein further comprising detecting the first target molecule in the tissue sample with the primary antibody by IHC. This disclosed embodiment comprises automatically dispensing a hapten-labeled nucleic acid probe onto the tissue sample under conditions sufficient for such probe to specifically bind a second target molecule. In some examples, the hapten-labeled nucleic acid probe comprises an electron-deficient aromatic compound as previously described. Further embodiments comprise treating the tissue sample with a solution containing an electron-rich aromatic compound prior to or concomitantly with automatically dispensing the second, hapten-labeled nucleic acid probe onto the tissue sample and detecting the second target molecule by ISH. In such embodiments, the electron-rich aromatic compound comprises a formula as previously described. In a particular embodiment, the electron-rich aromatic compound is a hydroxyl aryl or hydroxyl biaryl compound, such as naphthol. The naphthol concentration may vary, but typically ranges from approximately 0.1 to 10 milligrams per milliliter, approximately 0.2 milligrams per milliliter to 7 milligrams per milliliter, or approximately 0.3 milligrams per milliliter to 1 milligram per milliliter.

In one embodiment of the present method, automatically dispensing the hapten-labeled nucleic acid probe onto the tissue sample occurs after treating the tissue sample with an electron rich aromatic compound. In another embodiment, automatically dispensing onto the tissue sample a hapten-labeled nucleic acid probe occurs simultaneously with treating the tissue sample with an electron rich aromatic compound, in which the electron rich aromatic compound and hapten-labeled nucleic acid probe are applied to the tissue sample either substantially simultaneously or in the same solution. In some examples, the hapten-labeled nucleic acid probe is a hapten-labeled DNA probe, such as a DNP-labeled DNA probe.

In some embodiments of the present invention, IHC is performed prior to ISH. In other embodiments, ISH is performed prior to IHC. In some examples, ISH includes detecting the targeted nucleic acid by horseradish peroxidase silver staining or alkaline phosphatase red silver staining In some examples, IHC detection includes detecting the targeted protein by an alkaline phosphatase-red enzyme chromogen complex or a horseradish peroxidase-DAB enzyme chromogen complex.

The methods as disclosed herein can be performed manually or automatically, for example on an automated tissue processing instrument. Automated systems typically are at least partially, if not substantially entirely, under computer control. Because automated systems typically are at least partially computer controlled, certain embodiments of the present disclosure also concern one or more tangible computer-readable media that stores computer-executable instructions for causing a computer to perform disclosed embodiments of the method.

IV. Samples and Targets

Samples include biological components and generally are suspected of including one or more target molecules of interest. Target molecules can be on the surface of cells and the cells can be in a suspension, or in a tissue section. Target molecules can also be intracellular and detected upon cell lysis or penetration of the cell by a probe. One of ordinary skill in the art will appreciate that the method of detecting target molecules in a sample will vary depending upon the type of sample and probe being used. Methods of collecting and preparing samples are known in the art.

Samples used in the methods described herein, such as a tissue or other biological sample, can be prepared using any method known in the art. The samples can be obtained from subjects for routine screening or from subjects that are suspected of having a disorder, such as a genetic abnormality or a neoplasia. The described methods can also be applied to samples that do not have genetic abnormalities, diseases, disorders, etc., referred to as "normal" samples. Such normal samples are useful, among other things, as controls for comparison to other samples. The samples can be analyzed for many different purposes. For example, the samples can be used in a scientific study or for the diagnosis of a suspected malady, or as prognostic indicators for treatment success, survival, etc.

Samples can include multiple targets that can be specifically bound by a probe or reporter molecule. The targets can be nucleic acid sequences or proteins. Throughout this disclosure when reference is made to a target protein it is understood that the nucleic acid sequences associated with that protein can also be used as targets. In some examples, the target is a protein or nucleic acid molecule from a pathogen, such as a virus, bacteria, or intracellular parasite, such as from a viral genome. For example, a target protein may be produced from a target nucleic acid sequence associated with (e.g., correlated with, causally implicated in, etc.) a disease.

A target nucleic acid sequence can vary substantially in size. Without limitation, the nucleic acid sequence can have a variable number of nucleic acid residues. For example a target nucleic acid sequence can have at least about 10 nucleic acid residues, or at least about 20, 30, 50, 100, 150, 500, 1000 residues. Similarly, a target polypeptide can vary substantially in size. Without limitation, the target polypeptide will include at least one epitope that binds to a peptide specific antibody, or fragment thereof. In some embodiments that polypeptide can include at least two epitopes that bind to a peptide specific antibody, or fragment thereof.

In specific, non-limiting examples, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. Therefore, in some examples, at least a portion of the target molecule is produced by a nucleic acid sequence (e.g., genomic target nucleic acid sequence) amplified or deleted in at least a subset of cells in a sample.

Oncogenes are known to be responsible for several human malignancies. For example, chromosomal rearrangements involving the SYT gene located in the breakpoint region of chromosome 18q11.2 are common among synovial sarcoma soft tissue tumors. The t(18q11.2) translocation can be identified, for example, using probes with different labels: the first probe includes FPC nucleic acid molecules generated from a target nucleic acid sequence that extends distally from the SYT gene, and the second probe includes FPC nucleic acid generated from a target nucleic acid sequence that extends 3' or proximal to the SYT gene. When probes corresponding to these target nucleic acid sequences (e.g., genomic target nucleic acid sequences) are used in an in situ hybridization procedure, normal cells, which lack a t(18q11.2) in the SYT gene region, exhibit two fusion (generated by the two labels in close proximity) signals, reflecting the two intact copies of SYT. Abnormal cells with a t(18q11.2) exhibit a single fusion signal.

In other examples, a target protein produced from a nucleic acid sequence (e.g., genomic target nucleic acid sequence) is selected that is a tumor suppressor gene that is deleted (lost) in malignant cells. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

The aforementioned examples are provided solely for purpose of illustration and are not intended to be limiting. Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods, also include the EGFR gene (7p12; e.g., GENBANK™ Accession No. NC_000007, nucleotides 55054219-55242525), the C-MYC gene (8q24.21; e.g., GENBANK™ Accession No. NC_000008, nucleotides 128817498-128822856), D5S271 (5p15.2), lipoprotein lipase (LPL) gene (8p22; e.g., GENBANK™ Accession No. NC_000008, nucleotides 19841058-19869049), RB1 (13q14; e.g., GENBANK™ Accession No. NC_000013, nucleotides 47775912-47954023), p53 (17p13.1; e.g., GENBANK™ Accession No. NC_000017, complement, nucleotides 7512464-7531642)), N-MYC (2p24; e.g., GENBANK™ Accession No. NC_000002, complement, nucleotides 151835231-151854620), CHOP (12q13; e.g., GENBANK™ Accession No. NC_000012, complement, nucleotides 56196638-56200567), FUS (16p11.2; e.g., GENBANK™ Accession No. NC_000016, nucleotides 31098954-31110601), FKHR (13p14; e.g., GENBANK™ Accession No. NC_000013, complement, nucleotides 40027817-40138734), as well as, for example: ALK (2p23; e.g., GENBANK™ Accession No. NC_000002, complement, nucleotides 29269144-29997936), Ig heavy chain, CCND1 (11q13; e.g., GENBANK™ Accession No. NC_000011, nucleotides 69165054.69178423), BCL2 (18q21.3; e.g., GENBANK™ Accession No. NC_000018, complement, nucleotides 58941559-59137593), BCL6 (3q27; e.g., GENBANK™ Accession No. NC_000003, complement, nucleotides 188921859-188946169), MALF1, AP1 (1p32-p31; e.g., GENBANK™ Accession No. NC_000001, complement, nucleotides 59019051-59022373), TOP2A (17q21-q22; e.g., GENBANK™ Accession No. NC_000017, complement, nucleotides 35798321-35827695), TMPRSS (21q22.3; e.g., GENBANK™ Accession No. NC_000021, complement, nucleotides 41758351-41801948), ERG (21q22.3; e.g., GENBANK™ Accession No. NC_000021, complement, nucleotides 38675671-38955488); ETV1 (7p21.3; e.g., GENBANK™ Accession No. NC_000007, complement, nucleotides 13897379-13995289), EWS (22q12.2; e.g., GENBANK™ Accession No. NC_000022, nucleotides 27994271-28026505); FLI1 (11q24.1-q24.3; e.g., GENBANK™ Accession No. NC_000011, nucleotides 128069199-128187521), PAX3 (2q35-q37; e.g., GENBANK™ Accession No. NC_000002, complement, nucleotides 222772851-222871944), PAX7 (1p36.2-p36.12; e.g., GENBANK™ Accession No. NC_000001, nucleotides 18830087-18935219), PTEN (10q23.3; e.g., GENBANK™ Accession No. NC_000010, nucleotides 89613175-89716382), AKT2 (19q13.1-q13.2; e.g., GENBANK™ Accession No. NC_000019, complement, nucleotides 45431556-45483036), MYCL1 (1p34.2; e.g., GENBANK™

Accession No. NC_000001, complement, nucleotides 40133685-40140274), REL (2p13-p12; e.g., GENBANK™ Accession No. NC_000002, nucleotides 60962256-61003682) and CSF1R (5q33-q35; e.g., GENBANK™ Accession No. NC_000005, complement, nucleotides 149413051-149473128).

In other examples, a target protein is selected from a virus or other microorganism associated with a disease or condition. Detection of the virus- or microorganism-derived target nucleic acid sequence (e.g., genomic target nucleic acid sequence) in a cell or tissue sample is indicative of the presence of the organism. For example, the target peptide, polypeptide or protein can be selected from the genome of an oncogenic or pathogenic virus, a bacterium or an intracellular parasite (such as *Plasmodium falciparum* and other *Plasmodium* species, *Leishmania* (sp.), *Cryptosporidium parvum*, *Entamoeba histolytica*, and *Giardia lamblia*, as well as *Toxoplasma, Eimeria, Theileria*, and *Babesia* species).

In some examples, the target protein is produced from a nucleic acid sequence (e.g., genomic target nucleic acid sequence) from a viral genome. Exemplary viruses and corresponding genomic sequences (GENBANK™ RefSeq Accession No. in parentheses) include human adenovirus A (NC_001460), human adenovirus B (NC_004001), human adenovirus C (NC_001405), human adenovirus D (NC_002067), human adenovirus E (NC_003266), human adenovirus F (NC_001454), human astrovirus (NC_001943), human BK polyomavirus (V01109; GI:60851) human bocavirus (NC_007455), human coronavirus 229E (NC_002645), human coronavirus HKU1 (NC_006577), human coronavirus NL63 (NC_005831), human coronavirus OC43 (NC_005147), human enterovirus A (NC_001612), human enterovirus B (NC_001472), human enterovirus C (NC_001428), human enterovirus D (NC_001430), human erythrovirus V9 (NC_004295), human foamy virus (NC_001736), human herpesvirus 1 (Herpes simplex virus type 1) (NC_001806), human herpesvirus 2 (Herpes simplex virus type 2) (NC_001798), human herpesvirus 3 (Varicella zoster virus) (NC_001348), human herpesvirus 4 type 1 (Epstein-Barr virus type 1) (NC_007605), human herpesvirus 4 type 2 (Epstein-Barr virus type 2) (NC_009334), human herpesvirus 5 strain AD169 (NC_001347), human herpesvirus 5 strain Merlin Strain (NC_006273), human herpesvirus 6A (NC_001664), human herpesvirus 6B (NC_000898), human herpesvirus 7 (NC_001716), human herpesvirus 8 type M (NC_003409), human herpesvirus 8 type P (NC_009333), human immunodeficiency virus 1 (NC_001802), human immunodeficiency virus 2 (NC_001722), human metapneumovirus (NC_004148), human papillomavirus-1 (NC_001356), human papillomavirus-18 (NC_001357), human papillomavirus-2 (NC_001352), human papillomavirus-54 (NC_001676), human papillomavirus-61 (NC_001694), human papillomavirus-cand90 (NC_004104), human papillomavirus RTRX7 (NC_004761), human papillomavirus type 10 (NC_001576), human papillomavirus type 101 (NC_008189), human papillomavirus type 103 (NC_008188), human papillomavirus type 107 (NC_009239), human papillomavirus type 16 (NC_001526), human papillomavirus type 24 (NC_001683), human papillomavirus type 26 (NC_001583), human papillomavirus type 32 (NC_001586), human papillomavirus type 34 (NC_001587), human papillomavirus type 4 (NC_001457), human papillomavirus type 41 (NC_001354), human papillomavirus type 48 (NC_001690), human papillomavirus type 49 (NC_001591), human papillomavirus type 5 (NC_001531), human papillomavirus type 50 (NC_001691), human papillomavirus type 53 (NC_001593), human papillomavirus type 60 (NC_001693), human papillomavirus type 63 (NC_001458), human papillomavirus type 6b (NC_001355), human papillomavirus type 7 (NC_001595), human papillomavirus type 71 (NC_002644), human papillomavirus type 9 (NC_001596), human papillomavirus type 92 (NC_004500), human papillomavirus type 96 (NC_005134), human parainfluenza virus 1 (NC_003461), human parainfluenza virus 2 (NC_003443), human parainfluenza virus 3 (NC_001796), human parechovirus (NC_001897), human parvovirus 4 (NC_007018), human parvovirus B19 (NC_000883), human respiratory syncytial virus (NC_001781), human rhinovirus A (NC_001617), human rhinovirus B (NC_001490), human spumaretrovirus (NC_001795), human T-lymphotropic virus 1 (NC_001436), human T-lymphotropic virus 2 (NC_001488).

In certain examples, the target protein is produced from a nucleic acid sequence (e.g., genomic target nucleic acid sequence) from an oncogenic virus, such as Epstein-Barr Virus (EBV) or a Human Papilloma Virus (HPV, e.g., HPV16, HPV18). In other examples, the target protein produced from a nucleic acid sequence (e.g., genomic target nucleic acid sequence) is from a pathogenic virus, such as a Respiratory Syncytial Virus, a Hepatitis Virus (e.g., Hepatitis C Virus), a Coronavirus (e.g., SARS virus), an Adenovirus, a Polyomavirus, a Cytomegalovirus (CMV), or a Herpes Simplex Virus (HSV).

V. Sample Preparation

The tissue samples described herein can be prepared using any method now known or hereafter developed in the art. Generally, tissue samples are prepared by fixing and embedding the tissue in a medium.

In some examples an embedding medium is used. An embedding medium is an inert material in which tissues and/or cells are embedded to help preserve them for future analysis. Embedding also enables tissue samples to be sliced into thin sections. Embedding media include, but are not limited to, paraffin, celloidin, OCT™ compound, agar, plastics, or acrylics.

Many embedding media are hydrophobic; therefore, the inert material may need to be removed prior to histological or cytological analysis, which utilizes primarily hydrophilic reagents. The term deparaffinization or dewaxing is broadly used herein to refer to the partial or complete removal of any type of embedding medium from a biological sample. For example, paraffin-embedded tissue sections are dewaxed by passage through organic solvents, such as toluene, xylene, limonene, or other suitable solvents.

The process of fixing a sample can vary. Fixing a tissue sample preserves cells and tissue constituents in as close to a life-like state as possible and allows them to undergo preparative procedures without significant change. Fixation arrests the autolysis and bacterial decomposition processes that begin upon cell death, and stabilizes the cellular and tissue constituents so that they withstand the subsequent stages of tissue processing, such as for IHC or ISH.

Tissues can be fixed by any suitable process, including perfusion or by submersion in a fixative. Fixatives can be classified as cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation). Additives may also be included in the fixative, such as buffers, detergents, tannic acid, phenol, metal salts (such as zinc chloride, zinc sulfate, and lithium salts), and lanthanum.

The most commonly used fixative in preparing samples for IHC is formaldehyde, generally in the form of a formalin solution (4% formaldehyde in a buffer solution, referred to as 10% buffered formalin). In one example, the fixative is 10% neutral buffered formalin.

VI. Probes

As described above, a probe includes a targeting moiety and a label. The targeting moiety functions to both specifically bind to a target molecule and associate with a label, such that the target is detectable. The targeting moiety can be associated with the label indirectly or directly. A person of ordinary skill in the art will appreciate that the label can be any of a variety of molecules that are known to a person of ordinary skill in the art, such as chromogenic molecules (e.g., molecules producing a pigment or coloring matter) or fluorophores (e.g., a molecule that absorbs a photon and triggers the emission of another photon with a different wavelength). In some examples, the chromogenic molecules are not detectable until they are reacted with an enzyme and/or an additional substrate. The label is used to detect or visualize the probe-target complex.

One particular example of a probe is a hapten-labeled probe, such as a DNP-labeled nucleic acid probe. In particular embodiments of the disclosed methods, a DNP-labeled nucleic acid probe is used to detect a nucleic acid sequence, in which the DNP-labeled nucleic acid probe concentration ranges from 5 µg/ml to 15 µg/ml, such as from 10 µg/ml to 15 µg/ml. In certain embodiments, detection is facilitated by using anti-hapten monoclonal antibodies. For example, a hapten-labeled probe directed to a target nucleic acid sequence is administered in a manner effective for the probe to recognize the target. The sample is then subjected to hybridization, followed by addition of an anti-hapten monoclonal antibody comprising an enzyme molecule, followed by addition of a substrate/chromogenic complex for detection of the target/probe complex.

Targeting moieties can be designed to be directly conjugated to a label. Used in this way the targeting moiety/label complex (i.e., the probe) is contacted with the sample and the target is detected.

Targeting moieties can also be indirectly associated with a label. In some examples, a first targeting moiety is contacted with a sample. The targeting moiety can be either nucleic acid based or protein based. The targeting moiety can be conjugated to another moiety that is then bound for instance by a secondary antibody or a non-peptide based binding moiety, such as biotin. The secondary antibody or non-peptide binding pair can then be linked to a label. In another example, a targeting moiety can be indirectly associated with a label by conjugating the targeting moiety, either directly or indirectly, to a peptide having enzymatic activity. The enzymatic activity is chosen so that upon addition of a substrate(s) the substrate(s) is converted into a label, or becomes a more active label.

Exemplary non-limiting examples of enzyme/substrate pairs include the following: HRP/DAB; AP/Naphthol AS-TR phosphate (or Naphthol AS-MS phosphate, etc.); and beta-D-galactosidase (beta-D-Gal) with a chromogenic substrate (e.g., p-nitrophenyl-beta-D-galactosidase) or fluorogenic substrate (e.g., 4-methylumbelliferyl-beta-D-galactosidase). Numerous other enzyme-substrate combinations are known to those skilled in the art. For a general review of these, see U.S. Pat. Nos. 4,275,149 and 4,318,980. When a probe is made from the indirect association of one or more additional molecules, the additional molecules can be referred to as probe components.

As previously described, in some examples the label is indirectly conjugated with an antibody. For example, an antibody can be conjugated to biotin wherein biotin binds selectively to avidin for subsequent detection. Alternatively, an antibody is conjugated with a small hapten and a label is conjugated to an anti-hapten antibody. Thus, indirect conjugation of the label with the targeting moiety can be achieved.

When the probe includes an enzyme that reacts with a substrate to generate the detection label the substrate can be a chromogenic compound. There are numerous examples of such substrates. For example, many such compounds can be purchased from Invitrogen, Eugene Oreg. Particular non-limiting examples of chromogenic compounds include nitrophenyl-β-D-galactopyranoside (ONPG), 5-bromo-4-chloro-3-indolyl-β-galactopyranoside (X-Gal), methylumbelliferyl-β-D-galactopyranoside (MU-Gal), p-nitorphenyl-α-D-galactopyranoside (PNP), 5-bromo-4-chloro-3-indolyl-β-D-glucuronide (X-Gluc), and 3-Amino-9-ethylcarbazol (AEC). Additional chromophoric molecules, such as quantum dots, can be used as labels. Certain quantum dots are commercially available, such as from Life Technologies Corporation (Carlsbad, Calif.).

VII. Counterstaining

Counterstaining is a method of post-treating the samples after they have already been stained with agents to detect one or more targets, such that their structures can be more readily visualized under a microscope. For example, a counterstain is optionally used prior to coverslipping to render the immunohistochemical stain more distinct. Counterstains differ in color from a primary stain. Numerous counterstains are well known, such as hematoxylin, eosin, methyl green, methylene blue, Geimsa, Alcian blue, and Nuclear Fast Red.

In some examples, more than one stain can be mixed together to produce the counterstain. This provides flexibility and the ability to choose stains. For example, a first stain, can be selected for the mixture that has a particular attribute, but yet does not have a different desired attribute. A second stain can be added to the mixture that displays the missing desired attribute. For example, toluidine blue, DAPI, and pontamine sky blue can be mixed together to form a counterstain.

In one embodiment, cell conditioning may be completed in one phase for dual gene-protein staining or in more than one phase. The IHC portion of the assay may be performed before or after the ISH portion of the assay.

VIII. Imaging

Certain aspects, or all, of the disclosed embodiments can be automated, and facilitated by computer analysis and/or image analysis system. In some applications precise color ratios are measured. In some embodiments, light microscopy is utilized for image analysis. Certain disclosed embodiments involve acquiring digital images. This can be done by coupling a digital camera to a microscope. Digital images obtained of stained samples are analyzed using image analysis software. Color can be measured in several different ways. For example, color can be measured as red, blue, and green values; hue, saturation, and intensity values; and/or by measuring a specific wavelength or range of wavelengths using a spectral imaging camera.

One disclosed embodiment involves using brightfield imaging with chromogenic dyes. White light in the visible spectrum is transmitted through the dye. The dye absorbs light of certain wavelengths and transmits other wavelengths. This changes the light from white to colored depending on the specific wavelengths of light transmitted.

The samples also can be evaluated qualitatively and semi-quantitatively. Qualitative assessment includes assessing the staining intensity, identifying the positively-staining cells and the intracellular compartments involved in staining, and evaluating the overall sample or slide quality. Separate evaluations are performed on the test samples and this analysis can include a comparison to known average values to determine if the samples represent an abnormal state.

IX. Test Kits

Disclosed embodiments of the present invention provide, in part, kits for carrying out various embodiments of the method of the invention. Examples of such kits include those useful for cholesterol analyses, pregnancy kits, cancer diagnostic kits, etc. Test kits of the present invention typically have a first reagent, typically a solution containing a soluble, electron-rich aromatic compound, such as a soluble, electron-rich aromatic compound having a formula

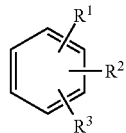

in which the R groups are as previously stated.

In a further example, the kit can have an electron-rich aromatic compound with $R^2$ and $R^3$ together form a fused aromatic ring having a formula

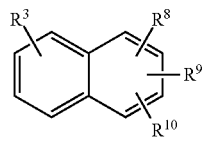

in which R groups are as previously stated. In a specific example, a kit includes a hydroxyl aryl or hydroxyl biaryl compound, such as naphthol, combined with hybridization solution and a hapten-labeled probe, such as a DNP-labeled nucleic acid probe.

The kit can include additional components, including antibodies, hapten-labeled probes and other reagents necessary for performing IHC and/or ISH by chromogenic detection. Such kits may be used, for example, by a clinician or physician as an aid to selecting an appropriate therapy for a particular patient or for diagnostic purposes.

X. Automated Embodiments

A person of ordinary skill in the art will appreciate that embodiments of the method disclosed herein for chromogenic detection of two or more molecules can be automated. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. published application Nos. 20030211630 and 20040052685, each of which is incorporated herein by reference. Particular embodiments of the procedures were conducted using various automated processes.

XI. Working Examples

The following examples are provided to illustrate certain specific features of working embodiments. The scope of the present invention is not limited to those features exemplified by the following examples.

Example 1

This example provides a staining assay that allows nucleic acids and protein to be detected in a single sample.

A. Material and Methods

Reagents utilized to perform the dual nucleic acid/protein hybridization and detection assays included the ULTRA-VIEW SISH Detection Kit (Ventana Medical Systems, Inc., p/n 780-001), the INFORM HER2 DNA Probe (Ventana Medical Systems, Inc., p/n 780-4332), the Rabbit Anti-DNP Antibody (Ventana Medical Systems, Inc., p/n 780-4335), the Rabbit Anti-HER2 (4B5) Antibody (Ventana Medical Systems, Inc., p/n 800-2996), and the ULTRAVIEW Universal Alkaline Phosphatase Red Detection Kit (Ventana Medical Systems, Inc., p/n 760-501). Standard bulk solutions were used on the BENCHMARK XT instrument. The NexES software programs were modified as needed to establish the order of addition of reagents, temperature and incubation times.

Tissues:

Dual hybridization and detection studies were performed on breast carcinoma tissues and xenograft material (HER2 3-in-1 Control Slides, Ventana Medical Systems, Inc., p/n 783-4332). Breast carcinoma tissue samples were screened for HER2 positive cells using the rabbit anti-HER2 (4B5) antibody and the HER2 DNA probe. Several cases were selected for use in multi-tissue blocks which were the main tissue models used for these studies. The multi-tissue blocks contained NBF-fixed tissue and Prefer-fixed tissue. Cases included 3+ as well as 1+ HER2 staining The 3+ cases showed genomic amplification while the 1+ cases showed normal genomic copy number. Qualified tissues were also used for TOP2A, EGFR, and c-Met DNA probes. The antibodies for these probes included TOP2A (51-8/5B4) Ki67 (30-9), EGFR (5B7), and c-Met (3D4), respectively.

Detection Systems:

The ISH portion of the assay was performed with the ULTRAVIEW SISH Detection Kit The IHC portion of the assay was performed with either the HRP-DAB system (ULTRAVIEW Universal DAB Detection Kit, Ventana Medical Systems, Inc., p/n 760-500) or the AP-Fast Red system (ULTRAVIEW Universal Alkaline Phosphatase Red Detection Kit, Ventana Medical Systems, Inc., p/n 760-501, and ULTRAVIEW Alkaline Phosphatase Red ISH Detection Kit, Ventana Medical Systems, Inc., p/n 800-504).

B. Results

Performance of IHC with the DAB detection system followed by ISH resulted in a significant amount of silver background staining that impaired further chromogenic signal detection. Initially it was thought that this background was due to the multimer-HRP conjugate found in the IHC DAB detection kit. Attempts to neutralize such activity by treating the tissue post-IHC detection with heat (60° C.-90° C. for 4 minutes) or hydrogen peroxide (3%) were unsuccessful. Adding silver detection reagents (Silver Chromagen A, B, and C from the SISH Detection Kit) post IHC showed no background. It was therefore concluded that the observed background was not due to the SISH detection reagents. No background was observed with the Rabbit anti-DNP antibody or the goat anti-rabbit-HRP conjugate. The DAB detection system for the IHC portion of the assay was changed to an Alkaline Phosphatase Fast Red detection system. While the Alkaline Phosphatase Fast Red detection system (either the ULTRAVIEW Universal Alkaline Phosphatase Red IHC and ISH Detection Kit) resulted in less silver background staining as compared with the DAB detection system, there were cases where background staining was still observed. Subsequent studies demonstrated that the background observed in conjunction with the DAB detection kit was due to the HER2 DNA probe.

Figure 1:
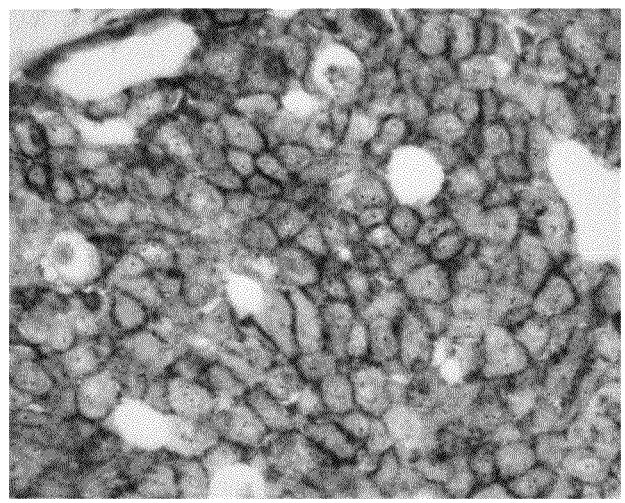
FIG. 1 is an exemplary microscopic (60×) view of a test sample with weak (1+) HER2 staining after IHC/ISH staining with the IHC Fast Red and SISH detection systems. This picture illustrates silver background staining following the pattern of the IHC stain making the red chromogen appear a different hue when silver speckled staining is present in the same location as the red chromogen.
Figure 3:
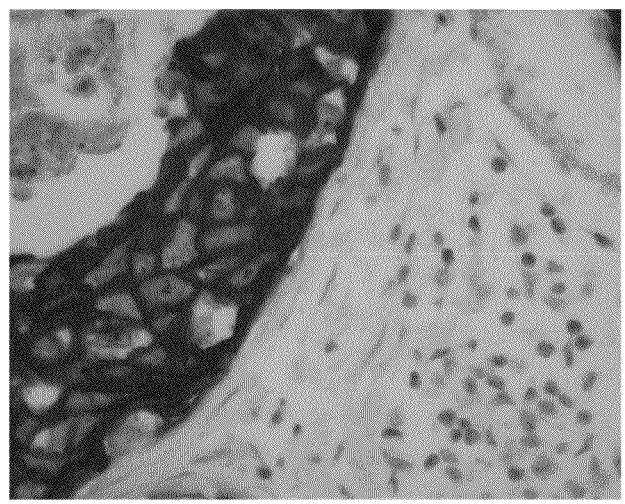
FIG. 3 is an exemplary microscopic (60×) view of a test sample with strong (3+) HER2 staining after IHC/ISH staining with the IHC Fast Red and SISH detection systems. This picture illustrates the absence of silver background staining in a sample with strong (3+) target staining.

Various amounts of silver background staining were observed in the IHC/ISH dual assay with both the DAB and Fast Red IHC detection systems. When the Fast Red detection system was used, the silver background followed the pattern of the IHC detection staining resulting in the red chromogen appearing a different hue when localized with silver speckled staining (see FIG. 1). This silver background was not always reproducible and it varied from instrument to instrument and from run to run making it difficult to trace to either instrument or reagent related causes. The silver background was not apparent with strong 3+ staining (see FIG. 3), but was significant with weak 1+ staining (see FIG. 1). Background appeared to increase with increased protease digestion prior to DNA probe hybridization.

The silver background associated with the Fast Red detection systems was initially thought to be due to cross reactivity of the goat anti-rabbit HRP binding to the rabbit anti-HER2 4B5 antibody and that this background could be reduced by using a post-IHC fixative step. However, when a negative control slide was assayed with the hybridization buffer minus the DNA probe there was no background staining, indicating that the background was not due to cross reactivity of the goat anti-rabbit HRP but due to the DNA probe itself.

Figure 4:
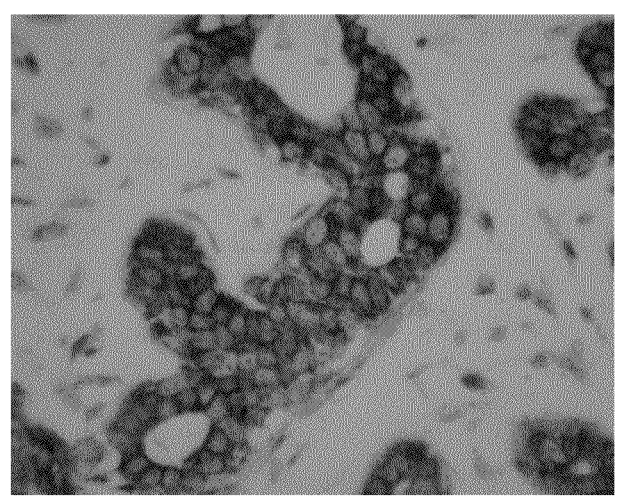
FIG. 4 is an exemplary microscopic (60×) view of a test sample with HPV III probe staining after HER2 antibody IHC Fast Red staining and HPV III probe (10 µg/mL) SISH detection systems. This picture illustrates silver background staining following the pattern of the IHC stain making the red chromogen appear a different hue when silver speckled staining is present in the same location as the red precipitated chromogen.
Figure 5:
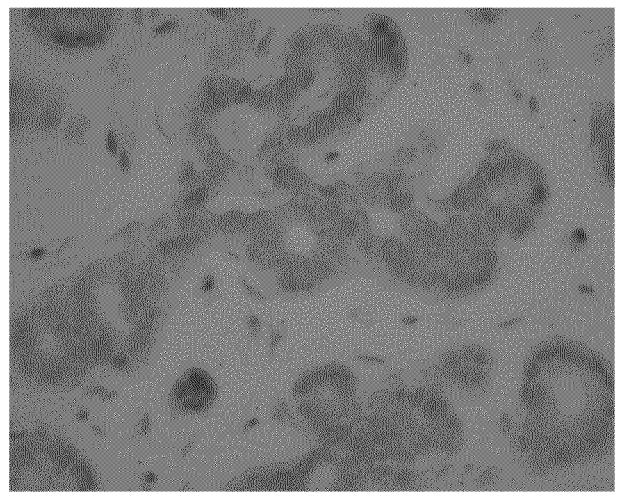
FIG. 5 is an exemplary microscopic (60×) view of a test sample after HER2 antibody IHC and ISH staining with a HPV FITC-labeled probe. This picture illustrates the absence of silver background staining in a sample when a probe is labeled with FITC instead of DNP.
Figure 6:
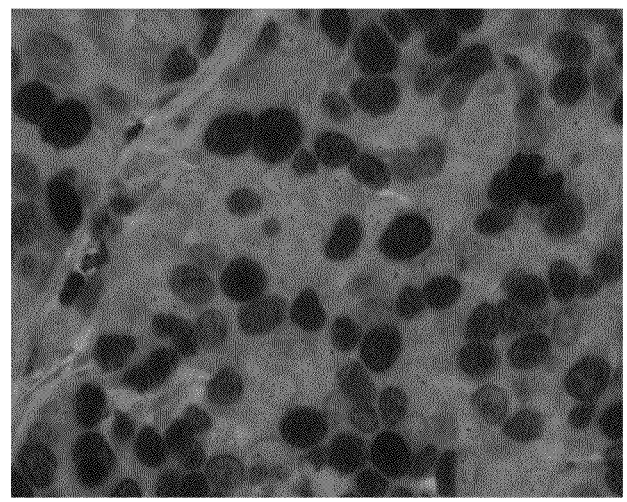
FIG. 6 is an exemplary microscopic (60×) view of a test sample (normal) after IHC/ISH staining with a Ki67 antibody (red) and TOP2A probe (silver). The TOP2A probe hybridization solution contained naphthol (300 µg/mL) allowing both Ki67 protein and nucleic acid sequences correlated with the Ki67 protein to be visualized with minimal background staining.
Figure 7:
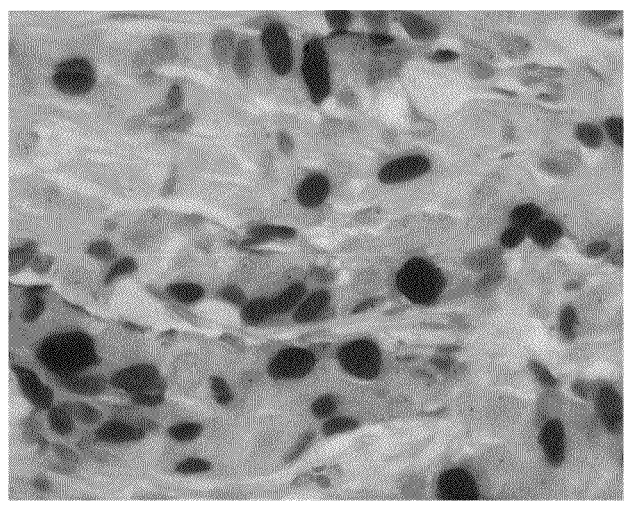
FIG. 7 is an exemplary microscopic (60×) view of a test sample (deletion) after IHC/ISH staining with a Ki67 antibody (red) and TOP2A probe (silver).
Figure 8:
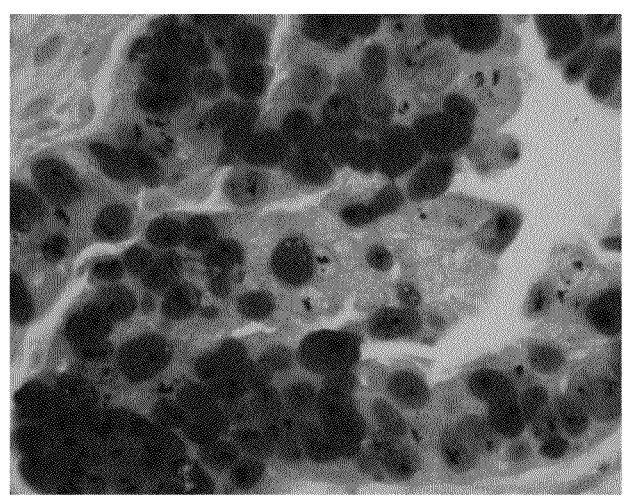
FIG. 8 is an exemplary microscopic (60×) view of a test sample (amplified target) after IHC/ISH staining with a Ki67 antibody (red) and TOP2A probe (silver), in which the TOP2A probe hybridization solution contained naphthol (300 µg/mL) allowing both protein and genes to be visualized with minimal background staining.
Figure 9:
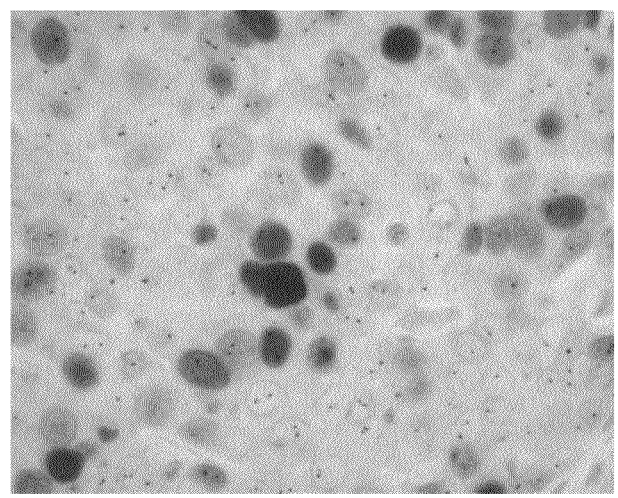
FIG. 9 is an exemplary microscopic (60×) view of a test sample (normal) after IHC/ISH staining with a TOP2A antibody (red) and TOP2A probe (silver), in which the TOP2A probe hybridization solution contained naphthol (300 µg/mL) allowing both the TOP2A protein and nucleic acid sequences correlated with the TOP2A protein to be visualized with minimal background staining.
Figure 10:
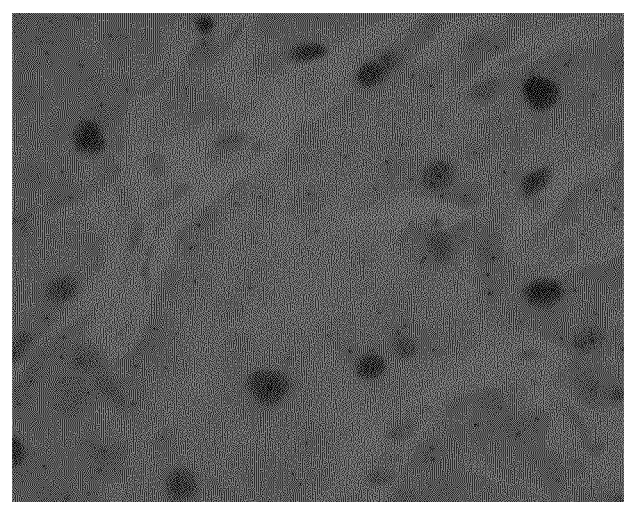
FIG. 10 is an exemplary microscopic (60×) view of a test sample (deletion) after IHC/ISH staining with a TOP2A antibody (red) and TOP2A probe (silver).
Figure 11:
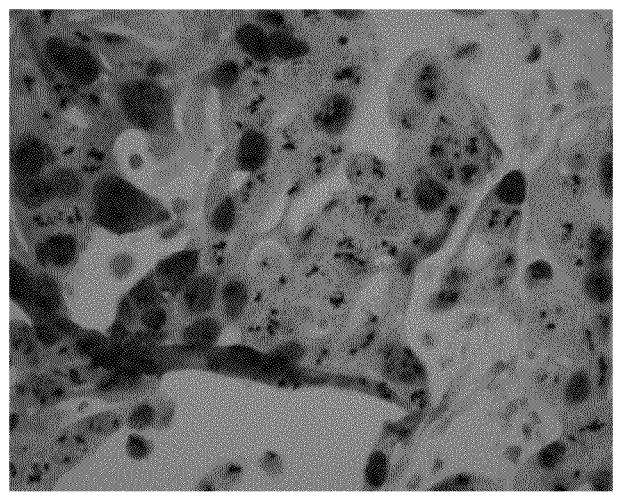
FIG. 11 is an exemplary microscopic (60×) view of a test sample (amplified) after IHC/ISH staining with a TOP2A antibody (red) and TOP2A probe (silver), in which the TOP2A probe hybridization solution contained naphthol (300 µg/mL) allowing both TOP2A protein and correlated nucleic acid sequences to be visualized with minimal background staining.
Figure 12:
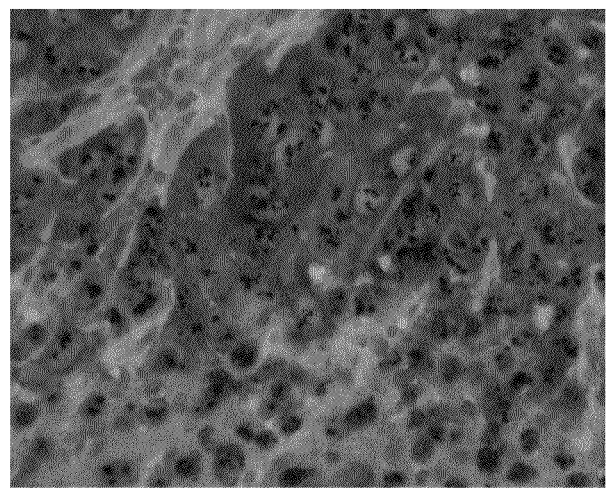
FIG. 12 is an exemplary microscopic (60×) view of a test sample (amplified target) after IHC/ISH staining with a EGFR antibody (red) and EGFR probe (silver), in which the EGFR probe hybridization solution contained naphthol (300

The silver background was also observed to be independent of the primary antibody. Antibodies such as those raised to CD20 and TOPOII also showed a silver background that followed the IHC staining pattern (CD20 is cytoplasmic on tonsil, TOPOII is nuclear). The silver background was also observed with different DNP-labeled DNA probes. Assays utilizing EGFR and TOPOII DNA probes in detection assays also demonstrated silver background. Assays utilizing an HPV III (16) DNA probe initially did not result in silver background, but when the concentration of the HPV prove was increased to the same level as that of the HER2 DNA probe (10 ug/mL), silver background was observed (see FIG. 4). Background was not observed with a FITC-labeled version of the HPV (16) DNA probe (see FIG. 5), indicating that the interaction was based on the DNP molecule interacting with the Fast Red/naphthol phosphate chromogen complex. Assays utilizing DNP labeled oligonucleotide probes specific for chromosome 7 and chromosome 17 did not contain silver background presumably because at 2 ug/mL the concentration was too low for this reaction to be observed.

One study was performed in which free DNP was incubated with tissue samples after the Fast Red chromogen development. The results from this study resulted in the same silver background associated with the Fast Red chromogen pattern.

Figure 2:
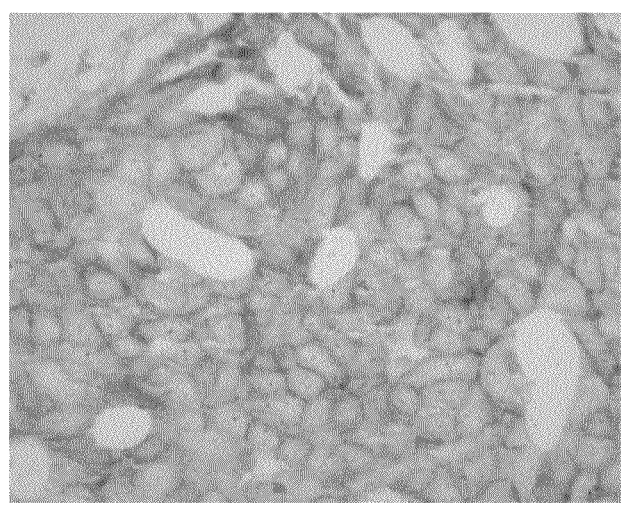
FIG. 2 is an exemplary microscopic (60×) view of a test sample with weak (1+) HER2 staining after IHC/ISH staining with the IHC Fast Red and SISH detection systems. This picture illustrates the absence of silver background staining in a test sample following treatment with naphthol prior to performing hybridization.

Competitive inhibition studies were conducted to determine if the silver background could be blocked by the addition of various chemicals to the slide in the presence of the DNA probes during probe hybridization. Blocking studies demonstrated that naphthol blocks silver background to at least trace levels (see FIG. 2). Naphthol was titrated in the hybridization buffer and found to block the silver background 100% at concentrations equal to or greater than 300 ug/mL in the dispenser. When the naphthol concentration was roughly 10 ug/mL or less there was no blocking of silver background, except at conditions of high pH (the pH of the hybridization solution was adjusted to pH 10). All of these results suggest that the DNP component on the DNP labeled probes binds primarily to the naphthol phosphate component in the Fast Red chromogen complex. This binding is significant at concentrations of DNP labeled probe of 10 ug/mL or greater.

Experiments were also performed using the TOP2A, EGFR, and c-Met DNA probes on tissue samples of amplified and non-amplified nucleic acid genomic sequences as well as a sequence deletion in the case of TOP2A (see FIGS. 6-13). The TOP2A DNA probe was hybridized with both TOP2A antibody and Ki67 antibody. In all instances, DNA probe hybridizations were detected along with antibody binding in the dual assays. The hybridization conditions included naphthol (300 ug/mL) thereby minimizing silver background contribution to the detection assays. These studies support methods for performing dual IHC/ISH hybridization and detection assays.

Example 2

Optimal Cell Conditioning

This example provides conditions for optimal cell conditioning for dual gene protein staining procedures.

A. Materials and Methods

Cell Conditioning: Optimal cell conditioning for each assay was determined by comparing different types of cell conditioning. Cell conditioning options included CC1 (Tris/Boric acid/EDTA, pH 8.6), CC2 (citric acid, pH 6.0), and a Reaction Buffer. The extent of cell conditioning was adjusted by selecting different times for cell conditioning, i.e., mild, standard, or extended. Tissue was also digested for ISH staining with either ISH protease 3 for approximately 4 minutes, protease 3 for approximately 8 minutes, or ISH protease 2 for approximately 4 minutes.

B. Results

Experiments were performed to determine the optimal cell conditioning conditions for anti-HER2 4B5 antibody staining according to the methods previously described. Optimal anti-HER2 4B5 antibody target detection was observed when the CC1 standard was selected. Staining was also achieved with CC2 and longer protease pretreatment as well as with Reaction Buffer. Although the staining was not as robust when CC1 was used, there was significant staining Reaction Buffer was the least effective solution for cell conditioning.

Experiments were performed to determine the optimal cell conditioning conditions for the HER2 DNA probe. The HER2 DNA probe performed optimally in target hybridizations when tissues were cell conditioned with CC2 at extended time, and when cell conditioning was supplemented with protease pretreatment. The longer the protease pretreatment, the greater the signal; however, too long of a protease pretreatment resulted in compromised tissue morphology (e.g., tissue degradation). Reaction Buffer was the least effective as a cell conditioning solution for DNA probe hybridization and detection.

These studies illustrate that basic cell conditioning (CC1 is Tris/Boric acid/EDTA pH 8.6) favors optimal anti-HER2 4B5 antibody IHC, whereas acidic cell conditioning coupled with protease digestion (CC2 is citric acid pH 6.0) favor DNA probe ISH. However, the HER2 protein antigen was able to withstand acidic cell conditioning, as cell conditioning with CC2 plus protease digestion produced a stronger IHC staining than CC2 alone.

At most pH levels histones are positively charged proteins due to the high lysine/arginine content. Lysine and arginine are amino acids with a high pKa (10.5 and 12.5 respectively) giving histones a pI in the pH range of 10.5-11.0. Most proteins have a pI in the pH range of 4.0-6.0. It is suggested that acidic (pH 6.0) cell conditioning is optimal for DNA probes because it is harsher on proteins than basic (pH 8.6) cell conditioning. Cell conditioning is basically denaturation with the breaking of covalent and non-covalent bonds that hold proteins together. Most proteins are subject to denaturation when the pH of the environment is close to the pI of the protein. Thus, when the pH is close to the pKa of that amino acid the normal electrostatic interactions between charged amino acid groups are weakened since a significant percentage will no longer be charged. Without the charge there is no electrostatic interaction. As a result, the protein will be less stable and more subject to denaturation, especially when the temperature is significantly elevated above 37° C.

For histones with a pI of 10.5 to 11.0, the electrostatic forces are largely unaffected since the pH will not be close to the pI. This means that the electrostatic forces will still be largely intact. Therefore, it is the surrounding proteins with a lower pI that will be most affected by the cell conditioning. As such, protease digestion to remove histones is best done under acidic cell conditioning to remove neighboring proteins as much a possible.

Example 3

Optimal Dual Gene/Protein Staining

This example illustrates that the IHC signal generated by the dual gene/protein staining procedure is dependent upon whether IHC is performed prior to or after ISH.

A. Materials and Methods

Cell Conditioning:
Optimal cell conditioning for each assay was determined as previously described.
Order of IHC and ISH:
The order of the two detection assays was determined by comparing ISH followed by IHC with IHC followed by ISH. The sequence of cell conditioning was also explored, whether to perform cell conditioning for each assay simultaneously, or sequentially.

B. Results

Experiments were performed to determine if the order of IHC and ISH influenced the IHC detection signal. It was found that the IHC detection signal was decreased if performed after ISH and better if IHC was done first. One explanation for this signal difference is the harsh conditions during hybridization where the temperature was increased to 95° C.

Even when IHC is performed prior to ISH, several formats for combining the two assays were tried. A few examples of these formats are shown in Table 1. Formats 1 and 2 were performed with adequate results, in that the ISH detection signal was good and IHC staining was observable but judged weaker (e.g., lower signal intensity) than results obtained from a single IHC assay. Tissue morphology was less optimal with protease 2 digestion.

It may be possible to do all the cell conditioning early in the IHC assay and perform protease digestion after IHC detection as described in Format 3. While it may be possible to generate both IHC and ISH signal with a number of different formats, a desirable format is one that generates the best signal and morphology compared to a single stain assay.

TABLE 1

Dual IHC/ISH procedure formats.

| Format 1 | Format 2 | Format 3 |
|---|---|---|
| Deparafinization | Deparafinization | Deparafinization |
| Cell Conditioning-CC1 | Cell Conditioning-CC1 | Cell Conditioning-CC1 |
| Primary Antibody | Cell Conditioning-CC2 | Cell Conditioning-CC2 |
| IHC Detection | Protease | Primary Antibody |
| Cell Conditioning-Rxn. Buffer | Primary Antibody | IHC Detection |
| Protease | IHC Detection | Protease |
| DNA Probe hybridization | DNA Probe hybridization | DNA Probe hybridization |
| ISH detection | ISH detection | ISH detection |
| Counterstain | Counterstain | Counterstain |

Example 4

Use of Naphthol AS-TR Phosphate to Block Interaction between DNP and DAB and DNP and Anthracotic Pigments This example illustrates that anthracotic pigment absorption of a DNP-labeled probe is blocked by co-incubation of Naphthol AS-TR phosphate with the DNP-labeled probe on a tissue sample. Further, the experiments demonstrate that the interaction between DNP and DAB is also blocked in assays comprising naphthol in the hybridization buffer.

Anthracotic pigment appearance was enhanced after SISH detection and interfered with signal interpretation. Therefore, the mechanism by which SISH detection enhanced the appearance of anthracotic pigments was investigated. DNP-labeled nick-translated DNA probes were found to associate with anthracotic pigments while DNP-labeled oligoprobes did not produce background staining attributed to anthracotic pigments. One possible explanation was that as oligoprobes are labeled with less DNP molecules compared to nick-translated probes, the binding of DNP-labeled oligoprobes to the anthracotic pigments does not produce significant background staining as the concentration of DNP is lower.

The chromogenic appearance of SISH assay signal and signal naturally associated with anthracotic pigments is very similar. As such alkaline phosphatase (AP)-based blue detection was used for detecting the ISH signal.

Naphthol AS-TR phosphate was dissolved in hybridization buffer (HybReady, ULTRAVIEW SISH Detection Kit, Ventana Medical Systems, Inc., p/n 780-001). The hybridization buffer containing Naphthol AS-TR phosphate was utilized for in situ hybridizations.

Following deparafinization of the tissue samples, approximately 100 µl of residual SSC remained on the slide. Approximately 300 µl of hybridization buffer containing naphthol AS-TR phosphate was applied onto the slide. Liquid coverslip (LCS)(Ventana Medical Systems, Inc.) was applied to the slide to prevent evaporation. Approximately 200 µl of DNP-labeled nick-translated HER2 DNA probe (Ventana Medical Systems, Inc., p/n 780-4332) or EGFR DNA probe (Ventana Medical Systems, Inc., p/n 800-4343) were applied onto the slide prior to denaturation. The samples were heated, nucleic acids denatured to single stranded molecules, and in situ hybridization was allowed to proceed. After hybridization and wash steps, rabbit anti-DNP antibody was applied, slides were rinsed, and rabbit anti-DNP antibody, HRP-labeled goat anti-rabbit or AP-labeled goat anti-rabbit antibodies were applied and the slides incubated and assayed for final detection by either Silver detection or Blue detection, respectively. The experiment was repeated until the silver background staining due to the binding of DNP to DAB or the anthracotic pigment was diminished. Decreases is silver background staining was correlated with increases in the concentration of Naphthol AS-TR phosphate in the hybridization buffer.

Addition of 10 mg/ml of Naphthol AS-TR phosphate in the hybridization buffer decreased silver background staining due to the DNP component of the DNA probe binding to the anthracotic pigment. 5 mg/ml of Naphthol AS-TR phosphate in the hybridization solution used resulted in a significant decrease in silver background.

FIG. 14 (left panel) demonstrates dual color in situ hybridization for EGFR and chromosome 7 centromere (CEN7) DNA probes. EGFR ISH signal was detected using EGFR DNP-labeled nick translated DNA probe and the AP-based blue detection while CEN7 ISH signal was detected using CEN7 DNP-labeled oligoprobes and AP-based red detection. The enhanced appearance of the anthracotic pigment is seen as dark blue clusters (left panel). When the DNP-labeled nick translation probe was omitted from the assay (middle panel), the anthracotic pigment was seen as black clusters (the natural appearance of the anthracotic pigments).

Anthracotic pigments are partially comprised of carbon particles which have been known to adsorb polycyclic aromatic hydrocarbons, such as naphthol. Thus, the use of a water soluble polycyclic aromatic hydrocarbon (such as naphthol) for blocking the non-specific binding of DNP to the anthracotic pigment was evaluated. When naphthol was included in the hybridization buffer for in situ hybridization with EGFR DNP-labeled nick-translation probes, the anthracotic pigments were seen as black clusters (FIG. 14, right panel). These studies demonstrate that binding of the probe to the anthracotic pigment was successfully blocked by co-incubation of naphthol with the DNP-labeled nick-translated DNA probe during hybridization.

Example 5

Elimination of SISH Detection Background after DAB IHC

This example illustrates that a high concentration of Naphthol AS-TR phosphate (25 mg/ml) in the hybridization buffer eliminates the chemical interaction between DAB and DNP, thereby eliminating the background staining generated from the SISH detection.

During the development of IHC and ISH dual and triple detection assays, significant amounts of background staining from SISH detection after DAB-based IHC detection was seen. The background may be a result of the binding of the DNP component of DNP-labeled nick-translated DNA probes to DNA in the nuclei and deposited DAB staining. DAB is electron rich and binds to DNA and thus DAB is a cancer causing agent. DNP is an electron-deficient aromatic molecule that can bind to the electron-rich DAB. It was contemplated that adding a competitive blocking electron-rich aromatic molecule (such as naphthol-AS-TR phosphate) would prevent the non-specific binding.

In this experiment, the target for the IHC detection assay was HER2 protein which is expressed at high levels in HER2 gene amplified cells. The targets for ISH detection assays were the HER2 gene region and chromosome 17 centromere (CEN17). The HER2 protein target was detected with anti-HER2 antibody and DAB based detection. The HER2 gene target region was detected with DNP-labeled nick-translated DNA probe and SISH detection system, while CEN17 target was detected with DNP-labeled oligoprobes and AP based red detection system. HER2 SISH nucleic acid detection after HER2 IHC produced high background staining in the nuclei of HER2 protein negative cells (FIG. 15, upper left panel) and in the cytoplasm, cell membrane, and nuclei of HER2 protein positive cells (FIG. 15, lower left panel). Various Naphthol AS-TR phosphate concentrations were tested to determine if the co-incubation of Naphthol AS-TR phosphate with the DNP-labeled probe for target identification could prohibit the binding of the DNP-labeled nick-translated DNA probe to DAB. In order to suppress the binding of DNP to DAB staining high concentrations (25 mg/ml) on the slide were required. When the blocking of DNP-labeled nick translated DNA probe binding to DAB naphthol AS-TR phosphate was successfully achieved, there was no significant silver background staining in the nuclei of HER2 negative cells (FIG. 15, upper right panel) and in the cell membrane, cytoplasm, and nuclei of HER2 positive cells (FIG. 15, lower right panel). By blocking the binding of DNP-labeled nick-translated DNA probe to DAB, all three targets, namely HER2 protein, HER2 gene, and CEN17, are all visualized on the same tissue section (FIG. 15, lower right panel).

These studies illustrate that a high concentration of Naphthol AS-TR phosphate (25 mg/ml) in the hybridization buffer eliminates the chemical interaction between DAB and DNP.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for chromogenic detection of two or more target molecules in a single tissue sample, comprising in sequential order:
    contacting the tissue sample with a first specific binding moiety that specifically binds a first target molecule;
    detecting the first target molecule in the tissue sample by depositing an insoluble, electron-rich aromatic chromogen product;
    treating the tissue sample with a solution comprising a soluble, electron-rich aromatic compound;
    contacting the tissue sample with a second, hapten-labeled specific binding moiety that specifically binds a second target molecule, where a hapten of the second, hapten-labeled specific binding moiety comprises an electron-deficient aromatic compound; and,
    detecting the second target molecule by depositing a second, insoluble chromogen product that is distinguishable from the insoluble, electron-rich aromatic compound deposited to detect the first target molecule, where treating the tissue sample with the solution containing the soluble, electron-rich aromatic compound reduces background due to non-specific binding of the hapten-labeled specific binding moiety to the insoluble electron rich compound deposited near the first target molecule.

2. The method of claim 1, where the soluble, electron-rich aromatic compound has a formula

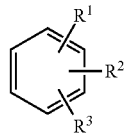

where at least one of $R^1$, $R^2$, $R^3$ are electron donating groups, independently selected from —$OR^4$, —$NR^6R^7$, —$OPO_3^{2-}$ and where $R^6$ and $R^7$ independently are H or lower alkyl or two of $R^1$, $R^2$ and $R^3$ together form a fused aromatic ring, optionally substituted with one, two or three electron donating substituents.

3. The method of claim 2, where $R^2$ and $R^1$ together form a fused aromatic ring, the electron rich aromatic compound having a formula

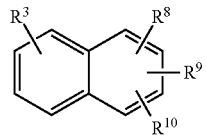

where $R^8$, $R^9$ and $R^{10}$ independently are selected from H, —$OR^{11}$, —$NR^{12}R^{13}$, —$OPO_3^{2-}$ or lower alkyl; and $R^{11}$, $R^{12}$ and $R^{13}$ independently are selected from H and lower alkyl.

4. The method of claim 1, where the soluble, electron-rich aromatic compound comprises naphthol.

5. The method of claim 4, where the naphthol concentration reduces background due to non-specific binding of the hapten-labeled specific binding moiety to the insoluble, electron-rich compound deposited near the first target molecule and ranges from 1 milligrams per milliliter to 30 milligrams per milliliter.

6. The method of claim 4, where the naphthol concentration ranges from about 1 milligrams per milliliter to about 7 milligrams per milliliter.

7. The method of claim 4, where the naphthol concentration ranges from about 0.3 milligrams per milliliter to about 1 milligrams per milliliter.

8. The method of claim 4, where the naphthol concentration ranges from about 0.3 milligrams per milliliter to about 1 milligrams per milliliter.

9. The method of claim 1, where the second, hapten-labeled specific binding moiety is a hapten-labeled nucleic acid probe.

10. The method of claim 9, where the hapten-labeled nucleic acid probe is a DNA probe.

11. The method of claim 10, where the hapten of the hapten-labeled nucleic acid probe is a nitroaryl compound.

12. The method of claim 11, where the nitroaryl compound is dinitrophenol.

13. The method of claim 12, where the concentration of the dinitrophenol nucleic acid-labeled probe is at least 5 µg/ml.

14. The method of claim 12, where the concentration of the dinitrophenol nucleic acid-labeled probe ranges from 10 µg/ml to 15 µg/ml.

15. The method of claim 1, where the hapten of the second, hapten-labeled probe is a nitroaryl compound.

16. The method of claim 15, where the nitroaryl compound is dinitrophenol.

17. The method of claim 1, where the first target molecule is a protein and the second target molecule is a nucleic acid sequence.

18. The method of claim 1, where the first target molecule is a protein and the second target molecule is a nucleic acid sequence that encodes the first target molecule protein.

19. The method of claim 17, where the protein is HER2/neu, c-Myc, n-Myc, Abl, EGFR protein, TOP2A, Bcl2, Bcl6, Rb1, p53, or c-Met.

20. The method of claim 1, where the second target molecule is a nucleic acid sequence.

21. The method of claim 20, where the nucleic acid sequence is a nucleic acid sequence encoding HER2, c-Myc, n-Myc, Abl, EGFR, TOP2A, Bcl2, Bcl6, Rb1, p53, c-Met.

22. The method of claim 1, where the first target molecule and second target molecule are a first protein and a second protein.

23. The method of claim 1, where the first target molecule and second target molecule are a first nucleic acid sequence and a second nucleic acid sequence.

24. The method of claim 1, where treating the tissue sample with the solution containing a soluble, electron-rich aromatic compound comprises treating the tissue sample with the solution containing a soluble, electron-rich aromatic compound prior to contacting the second, hapten-labeled specific binding moiety with the tissue sample.

25. The method of claim 1, where treating the tissue sample with the solution containing a soluble, electron-rich aromatic compound comprises treating the tissue sample with the solution containing a soluble, electron-rich aromatic compound concomitantly with contacting the second, hapten-labeled specific binding moiety with the tissue sample.

26. The method of claim 1, where the first specific binding moiety is a primary antibody.

27. The method of claim 26, where the primary antibody binds to HER2, c-Myc, n-Myc, Abl, EGFR protein, C-Met, TOP2A, Bcl2, Bcl6, Rb1, p53, or c-MET peptides.

28. The method of claim 1, where the insoluble, electron-rich aromatic compound comprises an azo dye.

29. The method of claim 1, where chromogenically depositing comprises reacting a substrate with a catalyst to directly or indirectly form the insoluble, electron-rich aromatic compound.

30. The method of claim 29, where the catalyst is an enzyme.

31. The method of claim 30, where the enzyme is alkaline phosphatase or horseradish peroxidase.

32. The method of claim 31, where the substrate is 3,3'-Diaminobenzidine (DAB), 3-Amino-9-ethylcarbazol (AEC), 4-Chloro-1-naphthol (4-CN), Naphthol AS-TR phosphate, 5-Bromo-4-chloro-3-indolyl phosphate (BCIP) or Nitrophenylphosphate (pNPP).

33. The method of claim 1, where detecting the first target molecule comprises performing immunohistochemistry (IHC) and detecting the second target molecule comprises performing in situ hybridization (ISH) in which performing IHC comprises detecting the first target molecule by an alkaline phosphatase-red chromogen detection system or a horseradish peroxidase-DAB chromogen detection system and performing ISH comprises detecting the second target molecule by a horseradish peroxidase silver ISH detection or an alkaline phosphatase red silver detection system.

34. The method of claim 1, where the method is automated.

35. The method of claim 1, wherein contacting the second, hapten-labeled specific binding moiety with the tissue sample is concomitantly with treating the tissue sample with the solution comprising the soluble, electron-rich aromatic compound.

* * * * *